US010960021B2

(12) United States Patent
Galloway et al.

(10) Patent No.: US 10,960,021 B2
(45) Date of Patent: Mar. 30, 2021

(54) METHOD OF TREATING A DISEASE USING A GLYCOLYTIC DEPENDENT COMPOUND

(71) Applicants: Ethicon, Inc., Somerville, NJ (US); Omrix Biopharmaceuticals Ltd., Rehovot (IL)

(72) Inventors: James Galloway, Bridgewater, NJ (US); Tamara Byk-Tennenbaum, Kiryat Ono (IL); Erez Ilan, Kibbutz Netzer Sereni (IL); Lior Weissman, Nes-Ziona (IL); Sivan Doron, Moshav Arugot (IL); Eve Montia, Rehovot (IL)

(73) Assignees: Omrix Biopharmaceuticals Ltd., Rehovot (IL); Ethicon, Inc., Somerville, NJ (US)

( * ) Notice: Subject to any disclaimer, the term of this patent is extended or adjusted under 35 U.S.C. 154(b) by 0 days.

(21) Appl. No.: 15/234,177

(22) Filed: Aug. 11, 2016

(65) Prior Publication Data
US 2017/0042930 A1 Feb. 16, 2017

Related U.S. Application Data

(60) Provisional application No. 62/205,031, filed on Aug. 14, 2015.

(51) Int. Cl.
| | | |
|---|---|---|
| A61F 2/00 | (2006.01) | |
| A61K 31/717 | (2006.01) | |
| A61K 31/704 | (2006.01) | |
| A61L 24/00 | (2006.01) | |
| A61L 15/28 | (2006.01) | |
| A61L 24/08 | (2006.01) | |
| A61L 15/44 | (2006.01) | |

(52) U.S. Cl.
CPC .......... *A61K 31/717* (2013.01); *A61K 31/704* (2013.01); *A61L 15/28* (2013.01); *A61L 15/44* (2013.01); *A61L 24/0015* (2013.01); *A61L 24/0042* (2013.01); *A61L 24/08* (2013.01); *A61L 2400/04* (2013.01)

(58) Field of Classification Search
None
See application file for complete search history.

(56) References Cited

U.S. PATENT DOCUMENTS

| | | |
|---|---|---|
| 3,364,200 A | 1/1968 | Ashton et al. |
| 4,626,253 A | 12/1986 | Broadnax, Jr. |
| 5,180,398 A | 1/1993 | Boardman et al. |
| 8,709,463 B2 | 4/2014 | Looney et al. |
| 2006/0104984 A1 | 5/2006 | Littlefield et al. |
| 2014/0274945 A1* | 9/2014 | Blaskovich .......... A61K 31/717 514/57 |

FOREIGN PATENT DOCUMENTS

| | | |
|---|---|---|
| WO | WO 2006/044879 | 4/2006 |
| WO | WO 2006/044882 | 4/2006 |

OTHER PUBLICATIONS

Pelicano et al. Oncogene. 2006; 25: 4633-4646.*
Nagy et al. British J. Cancer. 2009; 100: 865-869. (Year: 2009).*
Augustin R. "The protein family of glucose transport facilitators: It's not only about glucose after all" IUBMB Life. May 2010; 62(5) pp. 315-333.
Calvo M.B. et al. "Potential role of sugar transporters in cancer and their relationship with anticancer therapy". Int J Endocrinol. 2010, 14 pages.
Fournet S. et al. "False positive lymph node activity on positron emission tomography (PET/CT) due to hemostatic compresses" J Visc Surg. Apr. 2011;148(2):e153-155.
Ganapathy-Kanniappan S. et al "Tumor glycolysis as a target for cancer therapy: progress and prospects" Mol Cancer. 2013;12: 152 11 pages.
Holloway, R.W. et al 'Robotic-assisted resection of liver and diaphragm recurrent ovarian carcinoma: Description of technique' Gynecologic Oncology, vol. 120, No. 3 (2010) pp. 419-422.
Katzung, Bertram G. Basic & Clinical Pharmacology 9th Edition McGraw-Hill Medical. New York 2006. Chapter 55. 48 pages.
Madbouly, K.M. et al 'Regenerated oxidized cellulose reinforcement of low rectal anastomosis: Do we still need diversion?' Diseases of the Colon and Rectum, vol. 53, No. 6 (2010) pp. 889-895.
Medina R.A. et al. "Glucose transporters: expression, regulation and cancer" Biol Res. 2002;35(1) pp. 9-26, 23 pages.
Pelicano H. et al. "Glycolysis inhibition for anticancer treatment" Oncogene (2006) 25 pp. 4633-4646.
Shah K. "The role of glucose transporters in brain disease: diabetes and Alzheimer's Disease" Int J Mol Sci. 2012;13(10) pp. 12629-12655.
Shepherd P.R. et al "Glucose transporters and insulin action—implications for insulin resistance and diabetes mellitus" N Engl J Med. 1999;341(4) pp. 248-257.
Tokunaga, Y. et al 'Antitumor Effect of Oxycellulose as a Hemostatic during operation Introduction' Cancer Biotherapy & Radiopharmaceuticals vol. 1 (1998) Retrieved from the Internet: URL:http://online.liebertpub.com/doi/pdf/10.1089/cbr.1998.13.437.
Tommila M. et al Cellulose—A Biomaterial with Cell-Guiding Property Chapter 5 (2013) pp. 83-104.
Wang H and Chen P. "Surgicel® (oxidized regenerated cellulose) granuloma mimicking local recurrent gastrointestinal stromal tumor: A case report". Oncol Lett. May 2013;5(5):1497-1500.

(Continued)

*Primary Examiner* — David Browe
(74) *Attorney, Agent, or Firm* — David R. Crichton

(57) ABSTRACT

Provided is a method of enhancing toxicity of a glycolytic dependent compound towards a cell, tissue and/or organ e.g. a diseased cell, tissue and/or organ, the method comprises contacting Oxidized Regenerated Cellulose (ORC) and/or Oxidized Cellulose (OC); and a glycolytic dependent compound with the cell, tissue and/or organ. The ORC and/or OC; and the glycolytic dependent compound are contacted with the cell, tissue and/or organ in a non-blended form.

3 Claims, 1 Drawing Sheet

(56) References Cited

OTHER PUBLICATIONS

International Search Report re: PCT/US2016/046594 dated Oct. 24, 2016.
Written Opinion re: PCT/US2016/046594 dated Oct. 24, 2016.
Hwang, et al., Combined Effect of Interceed and 5-Fluorouracil on Delayed Adjustable Stabismus Surgery, J Ophthalmol, 1999, pp. 788-791, vol. 83.
Shiguang, Reports of 16 Cases, Chin J Min Inv Surg, 2013, pp. 806-809, vol. 13, No. 9.

* cited by examiner

METHOD OF TREATING A DISEASE USING A GLYCOLYTIC DEPENDENT COMPOUND

FIELD OF THE INVENTION

The invention relates to treating a disease using a glycolytic dependent compound in combination with Oxidized Regenerated Cellulose (ORC), and/or Oxidized Cellulose (OC). In one aspect, the invention relates to increasing selectivity of a cytotoxic glycolytic dependent compound towards a targeted pathological cell.

BACKGROUND OF THE INVENTION

Oftentimes, pathological tissues, especially malignant cells, present a particular challenge in treatment due to the fact that current therapies are not highly selective to cells displaying atypical cellular characteristics. Diseases such as Epilepsy, Diabetes, Psychosis, Parkinson's Disease, Depression, Malaria, and diseases caused by Bacteria, Viruses (e.g. HIV/Aids, Hepatitis B Virus) have been managed with therapies that are dependent on the glycolytic pathway for targeting and treating the pathology. Studies have shown that unregulated glucose transporters can manifest into commonly recognized diseases (Shepherd PR and Kahn BB. "Glucose transporters and insulin action—implications for insulin resistance and diabetes mellitus". N Engl J Med. 1999; 341(4):248-57; Shah K. "The role of glucose transporters in brain disease: diabetes and Alzheimer's Disease". Int J Mol Sci. 2012; 13(10):12629-55). Therapies that selectively target glucose transporters can be effective in managing pathologies where a disease involves a change in the transport of glucose or in glucose consumption level.

A malignant (cancer) cell is a cell that exhibits, or is predisposed to exhibit, unregulated growth. Understanding the biological differences between normal and cancer cells is essential for the design and development of anticancer drugs with selective anticancer activity (Pelicano H. et al. "Glycolysis inhibition for anticancer treatment". Oncogene (2006) 25, 4633-4646). It was reported that many types of tumors display high rates of glucose uptake. Different hypothesis were proposed to explain this exacerbated glucose consumption, including the increase of hexokinase expression, the decrease of glucose-6-phosphatasemediated glucose dephosphorylation and/or the overexpression of sugar transporters (Calvo MB et al. "Potential role of sugar transporters in cancer and their relationship with anticancer therapy". Int J Endocrinol. 2010). Also, it is increasingly evident that oncogenes and tumor suppressors regulate altered energy metabolism. Oncogenic mutations culminate in the up-regulation of glucose transporters (e.g. GLUT 1, GLUT 3) thus facilitating increased glucose consumption by cancer cells, which in turn increases the rate of glucose metabolism. Conversely, the glycolytic/metabolic phenotype confers selective advantage to cancer cells by supporting uninterrupted growth (Ganapathy-Kanniappan S and Geschwind J F. "Tumor glycolysis as a target for cancer therapy: progress and prospects". Mol Cancer. 2013; 12:152).

In contrast to normal differentiated cells that rely primarily on mitochondrial oxidative phosphorylation to generate the energy needed for cellular processes, most malignant cells rely on glucose breakdown for ATP generation. This phenomenon or glucose dependency is called "the Warburg effect". The dependency of malignant cells on glucose breakdown makes them vulnerable to compounds that are dependent on glycolytic transports/channels called "GLUTs" and/or compounds that target particular enzymes and pathways that are involved in the breakdown/processing of glucose molecules as their mechanism of action. Accordingly, one possible avenue of treatment for tumors involves glycolytic dependent therapies, which affect malignant cells by targeting cells that are using disproportionately large amounts of glucose for metabolism. Glycolytic therapies are chemotherapy drugs that are dependent on the metabolism of glucose for targeting cellular processes or enzymes. Target-specific agents have major advantages over the traditional chemotherapeutic compounds in that the targeting agents interact with the key molecular players in cancer cells and have low toxicity to normal cells (Pelicano H. et al.).

There are a number of different GLUTs and a number of compounds that target particular GLUTs for treatment. The majority of cancers over-express the GLUT family members which are typically present in the corresponding non-cancerous normal tissue. Oftentimes, cancer cells also express GLUTs which under normal conditions would not be present in these tissues. The localization, expression and regulation of the GLUT family are tissue and oftentimes cell-specific. A review on the regulation and expression of GLUT family members and research data on GLUT expression in human cancers and in isolated human cancer cell lines is summarized in Medina R A, Owen G I. "Glucose transporters: expression, regulation and cancer". Biol Res. 2002; 35(1): 9-26.

Examples of glycolytic Dependent therapies are: Imatinib/Brand name Gleevec (Protein Kinase Inhibitor, inhibits Hexokinase and G6PD activity); Daunorubicin-daunomycin/Brand name Cerubidine, DaunoXome (Amthracycline Topoisomerase Inhibitor); Cisplatin/Brand name Platinol, Platinol-AQ; Paclitaxel/Brand name Abraxane, Onxol (Microtubule Inhibitor); Doxorubicin/Brand name-Adriamycin, Doxil (Topoisomerase Inhibitor); 2-Deoxyglucose (Inhibits Hexokinase); Lonidamine (Inhibits glycolysis, mitochondrial respiration, and Hexokinase); 3-Bromopyruvate (Inhibits Hexokinase); Oxythiamine (Inhibits Pyruvate Dehydrogenase).

The above mentioned therapies are few examples of therapies that target particular enzymes and pathways that are necessary for cellular metabolism and function. Each of these therapies targets a particular stage of the cellular alterations thereby limiting the generation of energy/metabolism of the malignant cells, slowing growth and in many cases also leading to cell death. Sensitivity and specificity of glycolytic based therapies is dependent on metabolism of the therapies in cells. Cells that have high consumption of glucose are vulnerable to therapies that target enzymes and processes, involved in the breakdown/processing of glucose molecules. Typically, glycolytic therapies depend on the movement of glucose into the cells for their activity and are delivered systemically, with the intention that the compound will preferentially affect cancerous cells. However, there are a number of non-malignant cells and tissues in the human body that also use GLUTs for absorbing glucose for the production of ATP. Glucose transporters are found through a wide range of cells, in mammalian species. Cells that are particularly dependent on Glucose transporters for energy include the brain, retinal tissues, gonads, renal tissues, red blood cells etc. The dependence of some non-malignant cells on glucose makes them particularly vulnerable to therapies that target cellular processes or enzymes involved in the generation of energy. Even in cases where the malignant cells are absorbing large quantities there is still a quantity of the compound that is misdirected and absorbed by non-malignant tissues. This is problematic because the compounds are toxic to the tissues and cells they are absorbed to, resulting in cellular damage of non-malignant cells and in many side effects associated with chemotherapy and cancer treatments such as blindness, sterility, renal failure, pain, nausea and vomiting, fatigue, anemia, infections, etc.

Thus, there is a need to enhance delivery and targeting of therapies to pathological cells such as malignant cells, and increase the selectivity between the latter and normal cells.

Background art includes Agricultural and Biological Sciences, "Cellulose—Medical, Pharmaceutical and Electronic Applications", book edited by Theo van de Ven and Louis Godbout, ISBN 978-953-51-1191-7, Published: Aug. 29, 2013 under CC BY 3.0 license. Chapter 5 "Cellulose—A Biomaterial with Cell-Guiding Property" By Miretta Tommila, Anne Jokilammi, Risto Penttinen and Erika Ekholm, Pelicano H. et. al., Ganapathy-Kanniappan S and Geschwind J F., and Calvo M B et al.

SUMMARY OF THE INVENTION

In one aspect, the invention relates to a method of increasing targeting of cytotoxicity of a cytotoxic glycolytic dependent compound towards a pathological cell, e.g. a malignant cell, using Oxidized Regenerated Cellulose (ORC), and/or Oxidized Cellulose (OC).

In another aspect, the invention relates to a method of targeting a pathological cell e.g. a malignant cell using Oxidized Regenerated Cellulose (ORC) and/or Oxidized Cellulose (OC); and glycolytic dependent compound.

In another aspect, the invention relates to a method for increasing selectivity of a cytotoxic glycolytic dependent compound towards a pathological cell, e.g. a malignant cell, by using a combination treatment of: (i) Oxidized Regenerated Cellulose (ORC), and/or OC; and (ii) the cytotoxic glycolytic dependent compound, wherein the ORC/OC and the cytotoxic glycolytic dependent compound are administered by different administration routes and/or are administered in a non-blended form. In one embodiment, the combination treatment increases localization of a cytotoxic glycolytic dependent compound nearby a pathological cell and/or uptake of a cytotoxic glycolytic dependent compound into a pathological cell.

In another aspect, the invention relates to a method of enhancing toxicity of a glycolytic dependent compound towards a cell, tissue and/or organ for example a targeted cell, tissue and/or organ, the method comprises contacting Oxidized Regenerated Cellulose (ORC) and/or Oxidized Cellulose (OC); and a glycolytic dependent compound with the cell, tissue and/or organ; wherein the ORC and/or OC; and the glycolytic dependent compound are contacted with the cell, tissue and/or organ in a non-blended form.

According to the invention, toxicity of the glycolytic dependent compound can be enhanced by ORC/OC presence e.g. from 1.20-times and up to 5.00-times and also by sub ranges in between. Toxicity can be enhanced e.g. at least by 1.24, 1.30, 1.40, 1.50, 1.60, 1.66, 1.83, 1.89, 1.90, 1.92, 1.95, and by 2.00-times. In one embodiment, the toxicity is enhanced by at least 1.20-times or at least by 1.80-times in the presence of ORC and/or OC.

According to the invention the dose of the glycolytic dependent compound used in combination with ORC/OC is reduced by 1.20 and up to by 5.00-times (including sub ranges in between) as compared to the dose administered in the absence of ORC/OC. The dose can be reduced e.g. at least by 1.24, 1.30, 1.40, 1.50, 1.60, 1.66, 1.83, 1.89, 1.90, 1.92, 1.95, and 2.00-times as compared to the dose in the absence of ORC/OC. In one embodiment, the dose can be reduced at least by 1.20-times or at least by 1.80-times in the presence of ORC and/or OC as compared to the dose administered in the absence of ORC/OC.

In another embodiment, the ORC and/or OC is contacted with a cell, tissue and/or organ in a non-bleeding and/or non-resected site.

In another embodiment, the cell is a proliferating cell.

The term "toxicity" relates to the action of a chemical on the function of a cell, tissue and/or organ that can cause death, temporary incapacitation, or permanent harm.

The term "non-bleeding site" also includes a site, e.g. a resected bleeding site, in which prior to the contact/administration with ORC/OC the bleeding was reduced or substantially arrested e.g. by using a hemostatic agent other than ORC and/or OC such as fibrin sealant, commercially available gelatin based hemostat with or without thrombin.

In cell culture, a log (logarithmic) phase is a period of active cell proliferation (growing and/or multiplying), during which the number of cells increases exponentially. A proliferating cell in culture relates to cells in logarithmic growth. In one embodiment proliferating cell are cells growing up to less than 100% cell confluency such as 20%-30% cell confluency, 40%-50% cell confluency, 60%-70% cell confluency. "A proliferating cell", in-vivo and/or in culture, is a cell which is growing and/or multiplying.

A "blend" it is to be understood as any form of a mixture of ORC/OC and a cytotoxic glycolytic dependent compound before administration; a cytotoxic glycolytic dependent compound fixed, linked or bound to ORC/OC; and/or a cytotoxic glycolytic dependent compound and ORC/OC present in the same phase before administration, e.g. same liquid phase, same granular phase.

A "blend" it is to be understood as any form of a mixture of ORC/OC and a glycolytic dependent compound before administration; a glycolytic dependent compound fixed, linked or bound to ORC/OC; and/or a glycolytic dependent compound and ORC/OC present in the same phase before administration, e.g. same liquid phase, same granular phase.

When referring to a "non-blend", it is meant to exclude a "blend" as defined above. Non limiting examples of non-blend are non-fixed, non-linked, non-bound and/or not in the same phase before administration.

In another aspect, the invention relates to a method of treating a disease using a glycolytic dependent compound, the method comprising administering to a subject in need a therapeutically effective dose of Oxidized Regenerated Cellulose (ORC) and of a cytotoxic glycolytic dependent compound, wherein the ORC and the cytotoxic glycolytic dependent compound are administered by different administration routes and/or are administered in a non-blended form. In another aspect, the invention relates to a method of treating a disease using a glycolytic dependent compound, the method comprising administering to a subject in need a therapeutically effective dose of Oxidized Cellulose (OC) and of a cytotoxic glycolytic dependent compound, wherein the OC and the cytotoxic glycolytic dependent compound are administered by different administration routes and/or are administered in a non-blended form.

In another aspect, the invention relates to a method of treating a diseased cell, tissue and/or organ in a subject in need using a glycolytic dependent compound, the method comprising administering to the subject a therapeutically effective dose of Oxidized Regenerated Cellulose (ORC) and/or Oxidized Cellulose (OC); and of a glycolytic dependent compound, wherein the ORC and/or OC; and the glycolytic dependent compound are administered by different administration routes and/or are administered in a non-blended form.

In another aspect, the invention relates to a method of enhancing toxicity of a glycolytic dependent compound towards a cell, tissue and/or organ, the method comprises contacting Oxidized Regenerated Cellulose (ORC) and/or Oxidized Cellulose (OC); and a glycolytic dependent compound with the cell, tissue and/or organ; wherein the ORC and/or OC; and the glycolytic dependent compound are contacted with the cell, tissue and/or organ in a non-blended form.

In one embodiment, the toxicity is enhanced by at least 1.20-times or at least 1.80-times in the presence of ORC and/or OC.

In another embodiment, the ORC and/or OC is contacted with the cell, tissue and/or organ in a non-bleeding and/or non-resected site.

In another embodiment, the cell is a proliferating cell.

In another embodiment the ORC and/or OC is contacted with a diseased cell, tissue and/or organ.

In one embodiment, in view of the enhanced toxic effect of the glycolytic dependent compound by ORC/OC contact/presence, the dose of the glycolytic dependent compound is lower e.g. by 1.20-times or at least 1.80-times as compared to the dose administered in the absence of ORC/OC contact.

In one embodiment, in view of the enhanced toxic effect of the glycolytic dependent compound by ORC/OC contact/presence, a shortened period treatment time can be carried out (e.g. less treatment cycles and/or less treatment days per cycle) while using a the same dose as in the absence of ORC/OC contact.

In one embodiment, the glycolytic dependent compound is more effective locally, in the area where the ORC/OC is contacted with a diseased cell/tissue/organ.

In one embodiment, the period treatment time with the glycolytic dependent compound is reduced by at least 1.20-times or at least 1.80-times as compared with the same dose administered in the absence of ORC/OC contact/presence.

In one aspect provided is a kit comprising: a first separated container including a glycolytic dependent compound and a second separated container including ORC and/or OC and, optionally, instructions for use indicating that the ORC and/or OC; and the glycolytic dependent compound are administered by different administration routes and/or are administered in a non-blended form.

In certain aspects, provided is a kit comprising: a first separated container including a glycolytic dependent compound and a second separated container including ORC and/or OC and, optionally, instructions for use indicating that the ORC and/or OC; and the glycolytic dependent compound are administered in a non-blended form.

In one embodiment, the ORC and/or OC in the kit are included as an ORC and/or OC-coated surgical article and/or included within a surgical article.

In another aspect, the invention relates to a method of treating a disease using a glycolytic dependent compound and minimizing side effects, the method comprising administering to a subject in need a therapeutically effective dose of (i) Oxidized Regenerated Cellulose (ORC) and/or Oxidized Cellulose (OC); and (ii) of the cytotoxic glycolytic dependent compound, wherein the OC and the cytotoxic glycolytic dependent compound are administered in a non-blended form.

In certain embodiments, the invention relates to a method of treating a disease using a glycolytic dependent compound, the method comprising administering to a subject in need a therapeutically effective dose of ORC and/or OC; and of a glycolytic dependent compound, wherein the ORC and/or OC; and the glycolytic dependent compound are administered by different administration routes.

In some embodiments the ORC and/or OC are administered by a locoregional route and the glycolytic dependent compound is administered by a systemic route.

In one embodiment, the disease is cancer. In another embodiment, the therapeutically effective dose of the cytotoxic glycolytic dependent compound is lower than a standard dose administered in the absence of ORC and/or OC.

In another embodiment, the compound is administered for a shorter period of time as compared to the standard therapy used in the absence of ORC and/or OC.

In one embodiment, the ORC/OC is contacted with the diseased tissue cell and/or organ.

In one embodiment, the method minimizes side effects of a glycolytic dependent compound, e.g. due to a shorter exposure and/or lower dose of the glycolytic dependent compound.

In another aspect, the invention relates to use of Oxidized Regenerated Cellulose (ORC) and/or Oxidized Cellulose (OC); and a glycolytic dependent compound for treating a diseased cell, tissue and/or organ, wherein the ORC and/or OC; and the glycolytic dependent compound are for administration in a non-blended form.

In another aspect, the invention relates to use of Oxidized Regenerated Cellulose (ORC) and/or Oxidized Cellulose (OC); and a glycolytic dependent compound for enhancing toxicity of the glycolytic dependent compound towards a cell, tissue and/or organ, wherein the ORC and/or OC; and the glycolytic dependent compound are contacted with the cell, tissue and/or organ in a non-blended form.

In another aspect, the invention relates to Oxidized Regenerated Cellulose (ORC) and/or Oxidized Cellulose (OC); and a glycolytic dependent compound for use in a method of treating a diseased cell, tissue and/or organ, wherein the ORC and/or OC; and the glycolytic dependent compound are for administration in a non-blended form.

All aspects and embodiments relating to a glycolytic dependent compound described herein above and below also relate to a cytotoxic glycolytic dependent compound and/or to a cytostatic glycolytic dependent compound.

Also, all aspects and embodiments relating to a cytotoxic glycolytic dependent compound described herein above and below also relate to a cytostatic glycolytic dependent compound.

All aspects and embodiments relating to ORC described herein above and below also relate to OC.

All aspects and embodiments relating to OC described herein above and below also relate to ORC.

DESCRIPTION OF SOME EMBODIMENTS OF THE INVENTION

Figure 1:
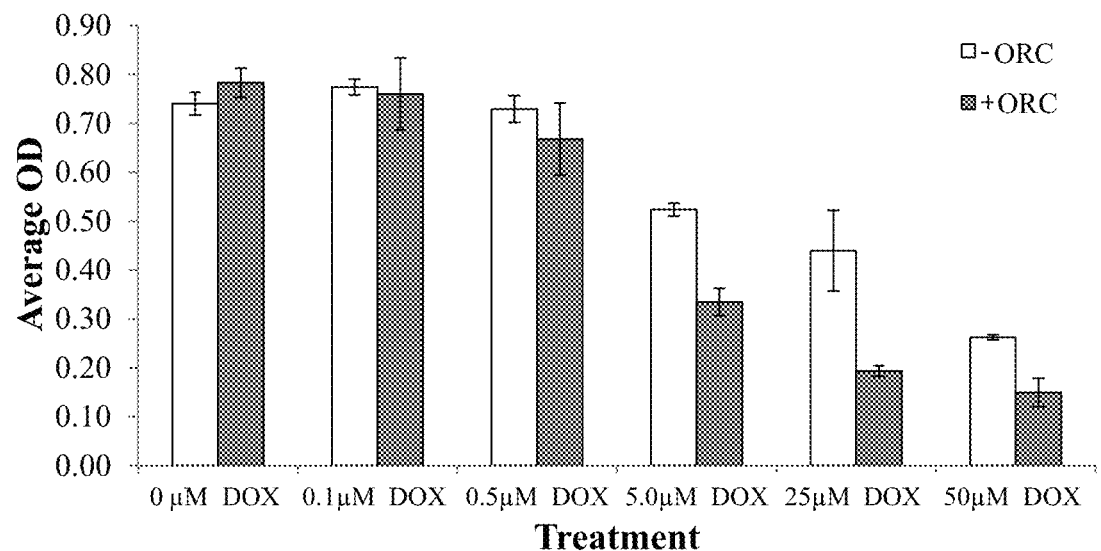
FIG. 1 shows average optical density (OD) values read at 450 nm and 650 nm of Normal Human Dermal Fibroblast (NHDF) cells stained with WST-1, which stains only metabolically active viable cells. The effect of Oxidized Regenerated Cellulose (ORC) and increasing concentrations of Doxorubicin (Dox) on NHDF cells viability was explored.

In one aspect, the invention relates to destroying a pathological cell using a dose of a cytotoxic glycolytic dependent compound (e.g. a chemotherapy drug, an antibiotic, an antiretroviral therapy that are glycolytic dependent) while the effect in non-pathological cells is minimal or non-existing e.g. following administration of the dose, at least 50% (e.g. and up to about 100%) of the non-pathological cells are viable and at least 55% (e.g. and up to about 100%) of the pathological cells are destroyed/non-viable (e.g. the cells do not maintain cellular functions). In one embodiment, the invention relates to selectively destroying a pathological cell by a combination treatment of (i) Oxidized Regenerated Cellulose (ORC) and/or Oxidized Cellulose (OC); and (ii) the cytotoxic glycolytic dependent compound.

The term "a pathological cell" refers to a cell that exhibits, or is predisposed to exhibit abnormal cellular alteration(s) that can be caused by a disease and/or are found in a disease such as Diabetes, Parkinson's Disease, Epilepsy, Psychosis, Depression, Malaria; a disease caused by Bacteria, Viruses (HIV/Aids, Hepatitis B Virus) or cancer. Abnormal cellular alteration(s) can be a change in the transport of glucose or in glucose consumption level.

Alternatively or in addition to abnormal glycolytic or glucose dependent alterations, pathological cells can display abnormal alterations in enzymatic activity critical for cellular functions which are not glycolytic or glucose dependent in nature. For example, pathologies in lysosomal activity (Lysosomal Storage Diseases LSD) affect the cells ability to digest large molecules which accumulate during cellular function. The accumulation of the molecules in the cell, eventually lead to cell death. Cystic Fibrosis is a disorder, which affects the transmembrane conductance regulator (CFTR). This results in the improper regulation of chloride ion channels, which are important in generating sweat, mucus, and enzymes for digestion. The buildup of excessive amounts of chloride prevents sodium resorption, which leads to blockage of organs which have secretions. Oftentimes, the cytotoxic glycolytic dependent compound inhibits cellular metabolism of the pathological cells by affecting specific enzymes necessary for cell proliferation and cellular hemostasis, leading to cell cycle arrest and apoptosis. "Apoptosis" (also called "the process of programmed cell death") is generally characterized by distinct morphological characteristics and energy-dependent biochemical mechanisms. Typically apoptosis is considered as a vital component of different cell processes such as normal cell turnover, proper development and functioning. Apoptosis may also occur in many human conditions including neurodegenerative diseases, ischemic damage, and many types of cancer.

In one embodiment, the pathological cell is a malignant cell (e.g. a cell tending or likely to grow and spread in a rapid and uncontrolled way and is oftentimes capable of metastasis, including a metastatic cell).

Within the context of this invention the term "dose" and "dosage" refer to a schedule regimen wherein one or multiple doses of the cytotoxic compound are administered during a pre-determined period of time. Table 1 appearing below lists examples of currently used dosage of several cytotoxic glycolytic dependent compounds. In the case of cancer the dose may depend on the cancer type and size and the patient's clinical condition.

The effective dose can be changed depending on the age and weight of the subject, the disease and its severity and other factors which can be recognized by the skilled in the art.

Clinically, a half-life of a given compound is the amount of time required for the compound to fall e.g. in the circulation to half its initial administered dose i.e. how long it takes for the body to remove half of the administered dose.

Typically, compounds are active for a multiple of their half-life, for example, five times the half-life can be used to describe the time period for a therapy's treatment. In the case of many therapies, this translates into days where the drug is having an effect on targeted tissues. All clinically used and approved drugs will have well described time ranges and amounts for calculating dose and therapy plans. In one embodiment, the performance of the compound in addressing the underlying pathology e.g. malignancy is adjusted in view of the presence of ORC, and/or OC that can localize the therapy at the target site during the limited time the compound is in the body and before it is being processed. Examples of a number of cytotoxic glycolytic dependent compounds and their respective half-lives are: Sunitinib having a half-life of about 41-86 hours, Sorafenib having a half-life of about 20-27 hours; Bevacizumab together with interferon (IFN) having a half-life of about 20 days; Everolimus having a half-life of about 30 hours; Temsirolimus having a half-life of about 17.3 hours; Pazopanib having a half-life of about 31 hours.

"A cytotoxic compound" refers to a medication/drug having a destructive and/or lethal effect on cells at a certain dose. Typically, cytotoxic compounds kill with first order kinetics (i.e. a dose will kill a constant proportion of the cell population). A compound with 99.9% killing efficiency may eliminate 3 log kill per dose. This may reduce a tumor mass of $10^9$ to $10^6$ cells. In one embodiment, a cytotoxic glycolytic dependent compound with 99.9% killing efficiency administered to a patient having a tumor mass of $10^9$ cells will result in a reduction of the tumor to a size of $10^6$ cells.

Typically, according to first order kinetics, a higher dose increases the log kill of the compound, therefore, increased targeting of first order drugs would be the equivalent of increasing systemic dose of non-targeted first order kinetic drugs.

"Glycolytic dependent compound" is a medication dependent on glycolytic transports/channels (GLUTs) i.e. a therapy that targets particular "GLUTs" for treatment and/or a medication that interrupts (e.g. decreases) the activity of metabolic enzymes. In one embodiment, the metabolic enzymes are those involved in the glycolytic pathway and in related energy-generating processes such as e.g. the citric acid cycle—also known as the tricarboxylic acid (TCA) cycle or the Krebs cycle; and the Fatty acid synthesis. Non limiting examples of such enzymes are Hexokinase, Phosphoglucose Isomerase, Phosphofructokinase, Glyceraldehyde 3 Phosphate Dehydrogenase, Phosphoglycerate Kinase (PGK), Phosphoglycerate mutase, Enolase, Glucose 6 Phosphate Isomerase, Phosphofructokinase, Alsolase, Triosephosphate Isomerase, Pyruvate Kinase, Pyruvate Dehydrogenase Complex, Citrate Synthesase, Isocitrate Dehydrogenase, Oxalosuccinate Decarboxylase, Glutarater Dehydrogenase Complex, Succinyl Thiokinase, Malate Dehydrogenase, Succinyl CoA Synthetase, Acetyl CoA: ACP Transacylase, 3 Ketoacyl ACP Reductase, Acetyl CoA Carboxylase, Acetoacetyl ACP, Glycerol 3-Phosphate. In one embodiment, the metabolic activity of Phosphoglycerate Kinase (PGK) is influenced by antiviral drugs e.g. Reverse transcriptase inhibitors such as Didanosine/Videx, Acyclovir/Zovirax, L-2'-deoxycytosine, L-2'-deoxythymidine.

In one embodiment, the metabolic activity of Glycerol 3-Phosphate is influenced by the antibiotic ascofuranone.

The term "glycolysis dependent therapy/therapies" refers to a treatment that uses a cytotoxic glycolytic dependent compound. The terms "cytotoxic glycolytic dependent compound", "cytotoxic glycolytic dependent molecule", "cytotoxic GLUT selective medication", "cytotoxic GLUT-dependent compound", "cytotoxic glucose transporter selective medication" are used herein interchangeably.

The term "glycolysis dependent therapy/therapies" is meant to include also cytostatic dependent therapy/therapies.

The term "cytotoxic compound" means a cell killing compound. The term "cytostatic compound" means a compound that slows and/or inhibits cell growth and/or cell multiplication.

Non limiting examples of a cytotoxic glycolytic dependent compound includes, but is not limited to, Imatinib (Gleevec), Daunorubicin or daunomycin (daunomycin cerubidine), and Cisplatin/paclitaxel, Doxorubicin/Adriamycin, ABT-737/ABT-263, Trastuzumab, Prednisolone, Oxaliplatin/5-FU, Prednisolone, Docetaxel, FK866, Paclitaxel, Trastuzumab, Sunitinib, Sorafenib, Bevacizumab with or without with IFN, Everolimus, Temsirolimus, Pazopanib, and combinations thereof.

"Cytotoxic glycolytic dependent compound" is also meant to include a combination of more than one cytotoxic glycolytic dependent compound e.g. combination of any of the above.

Non limiting examples of cytotoxic glycolytic dependent compounds that interrupt the activity of Tyrosine Kinase are: Imatinib/Gleevec, Bosutinib/Bosulif, Crizotinib/Xalkori, Dasatinib/Sprycel, Eriotinib/Tarceva, Lapatinib/Tykerb, Nilotinib/Tasigna, Sorafenib/Nexavar, Sunitinib/Sutent.

Non limiting examples of cytotoxic glycolytic dependent compounds that interrupt the metabolic activity of Topoisomerase II are: Daunorubicin/Cerubidine, Etoposide, Teniposide, Doxorubicin, Mitoxantrone, Amsacrine, Ellipticines, Aurintricarboxylic asid, HU-331, and Cannabidiol.

Non limiting examples of cytotoxic glycolytic dependent compounds that interrupt the metabolic activity of Glyceraldehyde 3-Phosphate Dehydrogenase are: Heptelidic Acid, CGP 3466B Maleate, FKBP36, Histone-Deacetylase-inhibitor 4-PB, Omigapil TCH346 or CGP3466. Non limiting examples of glycolytic dependent compounds that interrupt the metabolic activity of Pyruvate Kinase are: Cisplatin, Canertinib CI1033 and PKM2. Non limiting examples of glycolytic dependent compounds that interrupt the metabolic activity of Lactate Dehydrogenase are: Paclitaxel and Quinoline 3-Sulfonamids.

Non limiting examples of cytotoxic glycolytic dependent compounds that interrupt the metabolic activity of Pyruvate Dehydrogenase are: 5-FU/Adrucil, Sodium Dichloroacetate, Leelamine HCl, and Dichloroacetic acid.

TABLE 1

Examples of several currently used cytotoxic glycolytic dependent compounds, their doses and targeted metabolic enzyme.

| Drug Name | Targeted Metabolic Enzyme | Clinical Use | Pharmacokinetics | Dose* |
|---|---|---|---|---|
| Didanosine/Videx Acyclovir/Zovirax L-2'-deoxycytosine L-2'-deoxythymidine | Phosphoglycerate kinase (PGK) | Activation of HIV/AIDS antiretroviral drugs, HBV | Given orally on an empty stomach | 400 mg QD (one a day) (as capsules or tablets) |
| Imatinib/Gleevec | Tyrosine Kinase Inhibitor | Commonly used in the treatment of Chronic Myeloid Leukemia. | Given orally and is metabolized in the liver | 400-600 mg/d orally |
| Daunorubicin/ Cerubidine | Topoisomerase II | Commonly used in the treatment of Acute Leukemias | Given intravenously. Metabolized in the liver, and the products are excreted in the bile and the urine | 30-60 mg/m² daily IV for 3 days, or 30-60 mg/m² IV weekly |
| Cisplatin | Pyruvate Kinase | Cisplatin is commonly used as a component of regimens for testicular carcinoma and for cancers of the bladder, lung, and ovary | Cisplatin is used intravenously; the drug distributes to most tissues and is cleared unchanged by the kidneys | 20 mg/m²/d IV for 5 days or 50-70 mg/m² as single dose every 3 weeks |

TABLE 1-continued

Examples of several currently used cytotoxic glycolytic dependent compounds, their doses and targeted metabolic enzyme.

| Drug Name | Targeted Metabolic Enzyme | Clinical Use | Pharmacokinetics | Dose* |
|---|---|---|---|---|
| Doxorubicin/ Doxil | Topoisomerase II | Commonly used in Hodgkin's disease and in the treatment of myelomas, sarcomas, and breast, endometrial, lung, ovarian, and thyroid cancers | Given intravenously. Metabolized in the liver, and the products are excreted in the bile and the urine | 60 mg/m$^2$ daily IV for 3 days, or 30-60 mg/m$^2$ IV weekly |
| Paclitaxel | Lactate Dehydrogenase | Commonly used in advanced breast and ovarian cancers | Given intravenously | 130-170 mg/m$^2$ IV over 3 or 24 hours every 3-4 weeks |
| 5-FU/Adrucil | Pyruvate Dehydrogenase | Commonly used in bladder, breast, colon, head and neck, liver, and ovarian cancers | When given intravenously, widely distributed, including the cerebrospinal fluid | 15 mg/kg/d IV for 5 days by 24-hour infusion; 15 mg/kg weekly IV |

*The dose can be administered repeatedly multiple times.

In one aspect, the invention relates to increasing selectively of a cytotoxic glycolytic dependent compound towards a pathological cell (e.g. a malignant cell) by a combination treatment of Oxidized Regenerated (ORC), and/or OC; and the cytotoxic glycolytic dependent compound, wherein the ORC and the cytotoxic glycolytic dependent compound are administered by different administration routes and/or are administered in a non-blended form.

An increase in the selectivity level can be measured by comparing the lethal/cytotoxic effect of the cytotoxic glycolytic dependent compound on pathological cells versus the lethal effect of the glycolytic dependent compound on non-pathological cells.

An increase in selectivity level can be measured by comparing the lethal effect of the same dose of cytotoxic glycolytic dependent compound on pathological cells in the presence or the absence of ORC and/or OC.

In one embodiment, following daily intravenous administration of 60 mg/m$^2$ Doxil for 3 days, at least 51% of the malignant cells are destroyed in 3 days whereas the non-malignant cells remain substantially viable (at least 50% are viable). Following daily intravenous administration of 60 mg/m$^2$ Doxil for 3 days with the addition of ORC e.g. contacting the malignant cells at least 99% of the malignant cells are destroyed within 3 days whereas the effect in non-malignant cells is minimized (at least 55% are viable). In one embodiment, using a dose of the cytotoxic glycolytic dependent compound results in at least 1.5-times destruction (e.g. 2-times) of the malignant cells in the presence of ORC, and/or OC as compared to the destruction in their absence.

The treatment effect can be measured by using Computed Tomography (CT) and/or Positron Emission Tomography (PET) imaging following an injection of 18 Flurodeoxyglucose (18FG/18FDG, 18F, 18F-FDG, 18F-FDG) solution to a patient treated according to the invention and analyzing the cancer size and location. Typically, the change in 18FG uptake following treatment (as compared to an uptake before treatment) is an indication that the therapy is affecting the pathological cell (e.g. malignant cell) growth. The hyper metabolic state of the pathological cells allows 18FG to serve as a reliable marker for analyzing the metabolic activity of pathological cells especially, malignant cells. 18FG is a glucose analogue radioactive material that is preferentially absorbed by cells that are processing glucose rapidly in a tissue or organ. 18FG concentrates in highly metabolic cells due to their disproportionate use of Glucose breakdown for energy generation. The high sensitivity and specificity of 18FG to these highly active glycolytic cells makes it a reliable marker for identifying and monitoring malignant cells in radiographic studies. 18FG can be used to provide important information for patient management. For example, 18FG can be used to follow a patient's course of treatment e.g. through analysis of the cancer size on imaging studies. Typically, the absorption of 18FG relies on and is correlated with the presence of class 1 glucose transporters/channels including the classical transporters, GLUT1, GLUT4, GLUT3, GLUT14, and GLUT2 Augustin R. "The protein family of glucose transport facilitators: It's not only about glucose after all". IUBMB Life. 2010 May; 62(5): 315-33).

In one embodiment, following effective treatment of a malignancy or pathology with cytotoxic glycolytic dependent therapies, anticancer therapies, chemotherapy, therapeutics, etc., the pathological or malignant cells will be destroyed/killed. Death of the cells will be reflected by a drastic effect on the metabolic activity signal provided by 18FG in the tissue in which the cells are dying. If there is complete remission of the pathological tissues, there will be reduced uptake or no uptake of the glycolytic contrast (18FG) because there is reduced or no metabolic consumption of Glucose. Thus, 18FG uptake can be followed to assess the efficacy of a particular therapy in targeting particular tissues.

In this case diagnostic methods for analyzing cancer size/presence other than 18FG imaging may be more accurate. Other methods for measuring the lethal effect on malignant cells include particular markers for cancer cells such as Cancer Antigen 125 (CA 125 antigen), Alpha-fetoprotein (AFP), carcinoembryonic antigen (CEA), Cancer Antigen (CA19.9), S100, Lactate Levels, White blood cells (WBC), Red Blood Cell (RBC), to name a few. Effects of the lethal therapies on non-malignant cells can also be assessed based on the type of therapeutic being used. For example, cytotoxic glycolytic therapeutics can affect non-malignant cells that are reliant on glucose for energy, such as retinal cells, gonadal tissues, cardiac cells, etc. These organ systems can be monitored for loss of function to assess the effects of therapy on non-malignant cells. Viability/cell death can also be assessed by Nucleus Staining using dyes such as propidium iodide (PI), ethidium bromide (EB), diaminophenylindole (DAPI), acridine orange (AO), Hydrogenases, and Hoechst and/or mitochondrial function such as by measuring ATP synthase.

In one embodiment, a combination treatment includes contacting pathological cells (e.g. malignant cells) in a patient with Oxidized Regenerated Cellulose (ORC), and/or OC; and administering to the patient a glycolytic dependent compound e.g. a cytotoxic glycolytic dependent compound. The compound can be administered before, during, concurrently and/or after the contact of the pathological cells with ORC and/or OC.

For example, provided herein is a method for increasing selectively of a cytotoxic glycolytic dependent compound towards a pathological cell e.g. malignant cell in a patient, the method comprising contacting the pathological cell with Oxidized Regenerated Cellulose (ORC) and/or OC; and administering to the patient the cytotoxic glycolytic dependent compound, wherein the ORC and the cytotoxic glycolytic dependent compound are administered by different administration routes and/or are administered in a non-blended form. The treatment regimen may comprise a mixture of several cytotoxic glycolytic dependent compounds administered in parallel and/or one after the other. The treatment regimen may comprise several cytotoxic glycolytic dependent compounds administered in parallel and/or one after the other; and/or administration of other medications or therapies (such as radiation) with cytotoxic glycolytic dependent compound(s). In one embodiment, in the case of malignancy, studies have demonstrated that co-administration of N-(phosphonacetyl)-1-aspartate (PALA), 6-methylmercaptopurine riboside (MMPR), and 6-aminonicotinamide (6-AN) is an effective ATP-depleting regimen that increases the anticancer activity of radiation, and the cytotoxic glycolytic dependent compounds adriamycin, or taxol (Pelicano H. et al. pg. 4642). Also, co-administration of several cytotoxic glycolytic dependent compounds: glycolytic inhibitor 2-deoxyglucose with adriamycin or paclitaxel resulted in a significant increase of in vivo therapeutic activity in animal tumor models bearing osteosarcoma or non-small-cell lung cancer xenografts (Pelicano H. et al. pg. 4640) [Pelicano H. et al. "Glycolysis inhibition for anticancer treatment". Oncogene (2006) 25, 4633-4646].

The invention also relates to a method of cancer treatment with a cytotoxic glycolytic dependent compound in a patient, comprising: delivering e.g. by a systemic route, such as intravenous (IV) route or an oral route, the cytotoxic glycolytic dependent compound into the patient; and contacting Oxidized Regenerated Cellulose (ORC), and/or OC with the cancerous cells, tissue and/or organ thereby increasing sensitivity of the cancerous cells, tissue and/or organ to the compound.

The cytotoxic compound can be administered/delivered in any suitable and/or conventional mode, as long ORC/OC is administered by a different administration rout, including, but not limited to, topically, orally, intravenously, intramuscularly, cutaneously and subcutaneously. In one embodiment, the compound is administered systematically via enteral administration or parenteral administration (e.g. injection, infusion).

The term "contacting" includes, but is not limited to, being in proximity to (e.g. at a distance of about 1-10 cm), adjacent to (e.g. at a distance of about 0.001-1 cm), and being in direct connection e.g. touching and/or within the pathological cells. The term "contacting" is also meant to include placing the ORC, and/or OC in a superficial site not in direct proximity to the pathological cells, diseased tissue and/or diseased organ; and/or placing the ORC/OC at a locoregional location with respect to the treatment site e.g. in contrast to systemic on the one hand and local on the other.

In one embodiment, the ORC and/or OC is implanted in a patient in a superficial site not in direct proximity to the treatment site. In another embodiment, the ORC and/or OC is implanted in a patient in a superficial site not in direct proximity to the pathological cells, diseased tissue and/or diseased organ. In another embodiment, the ORC and/or OC is implanted in the patient in a superficial site not in direct proximity to the treatment site e.g. a surgical site following tumor resection. Such embodiments could be used in patients that the ORC effect on glycolytic therapies is not desired to be local but rather locoregional. Alternatively or additionally, the ORC and/or OC can be placed in close proximity or in direct connection with the pathological cell, diseased tissue and/or diseased organ.

The amount of applied ORC and/or OC is typically dependent on the intraoperative and postoperative effect desired by the surgical team. Cancer size and anatomical location would likely affect the quantity and form of ORC and/or OC placed. Furthermore, the surgical approach may impact how the surgical team is able to access tissues and may limit placement of ORC/OC.

ORC/OC can be delivered to a desired location by open surgery or minimal invasive procedure (MIS) such as laparoscopy. In one embodiment of the invention, an incision is made at the site of surgery and ORC/OC is applied to the desired site. The patient can receive local, regional or general anesthesia. The term "open surgery" refers to surgery wherein the surgeon gains direct access to the surgical site by a relatively large incision.

As used herein the term "minimally invasive procedure" means a surgery wherein the surgeon gains access to the surgical site via small incisions or through a body cavity or anatomical opening e.g. via laparoscopy. Accessory products (such as a trocar, graspers tweezers) may assist in the placement of ORC/OC in more challenging minimally invasive surgical approaches.

Any material/structure of ORC/OC can be used e.g. on, in or as a pad, powder, foam, liquid, paste and/or fabric, may be placed in the tumor bed (or site of tumor removal, site of metastatic concern, site of lymphatic drainage, etc.) before closing a surgical site. ORC/OC can be placed following partial or complete tumor resection or at a site e.g. close to or at the tumor place wherein tumor resection was not carried out.

The ORC/OC can be administered before, during, concurrently and/or after the compound e.g. cytotoxic compound as long as they are administered by different administration routes and/or are administered in a non-blended form. ORC/OC can be administered in a bleeding or non-bleeding surface such as a cancer cell, diseased tissue or organ. The ORC/OC can be administered into a patient's body. The ORC/OC can be placed in any suitable and/or conventional mode, including, but not limited to, topically, orally, intramuscularly, cutaneously and subcutaneously. In one embodiment, the compound is administered systematically via enteral administration or parenteral administration (e.g. injection, infusion).

The invention also relates to a method of treating a cancer patient having a malignant cell e.g. a malignant cell sensitive to a cytotoxic glycolytic dependent compound, the method comprising the steps of: administering to the patient a combination of ORC/OC and the cytotoxic glycolytic dependent compound. "A cell sensitive to a compound" means that exposure of the cell to a certain dose of the compound will result in impaired cell function, metabolism or cell destruction. The term "a cell sensitive to a compound" is interchangeable with the term "a cell vulnerable to a compound".

In one embodiment, following daily intravenous administration of 60 mg/m$^2$ cytotoxic glycolytic dependent compound for 3 days, at least 51% sensitive cells are destroyed in 3 days.

The term "malignant cell" refers to a cell characterized by progressive, abnormal, uncontrolled, invasive and/or metastatic growth; and is also meant to include a cell that is predisposed to exhibit unregulated, abnormal, invasive and/or metastatic growth.

"Malignant cell" is interchangeable with the terms "cancerous cell", "metastasic cell" and "cancer cell", and includes a neoplastic cell such as a premalignant cell and any cancerous/malignant tissue of a subject, for example, tumors, such as sarcomas and carcinomas (e.g. small cell lung cancer, and ovarian cancer), germ cell tumors; solid malignant tumors; metastasis or secondary cancer. Cancers which can be treated by using the disclosed combination methods include, but are not limited to, melanoma, hematological malignancies (blood cancers, like leukemia and lymphoma), plasmocytoma, breast cancer, sarcoma, glioma, thymoma, ovary cancer, prostate cancer, colon cancer, esophageal cancer, testicular cancer, leukemia, brain cancer, hepatoma, lung cancer, cervical cancer, and other neoplasms known in the art and metastases tumors thereof that have spread to other cells/tissue/organs. Treatments for pathologies that may not be centralized or fixed to a particular site, such as certain types of leukemia, may be dependent on the precise targeting of therapy to the underlying pathological tissues. For example, induction therapy for leukemia patients targets cells in the blood and bone marrow. Glycolytic dependent therapies used to target bone marrow sites in a patient (such as the pelvis, vertebrae, epiphyseal ends of the long bones, etc.) could be enhanced with the contact or approximation of ORC and/or OC with these bone marrow sites. ORC and/or OC could be incorporated into the treatment method to enhance the effectiveness of the glycolytic dependent therapies to the areas of the patient's body that are known to be affected by the underlying pathology being treated—in this case leukemia. For example, ORC and/or OC could be surgically implanted during bone marrow biopsies, to increase targeting of glycolytic therapies to a site of clinical significance to the underlying condition. The term "solid malignant tumor" is defined as a mass of malignant tissue whose cells have lost resemblance to normal cells, and that is characterized by aberrant, pathological and invasive growth into normal tissue.

Pathologies such as Leukemias, which are often not localized to a single anatomical location, can also be managed using glycolytic dependent therapies. In these clinical cases, the use of ORC and/or OC in anatomical locations in proximity to the affected tissues could be applied to assist in localizing a therapy. The locoregional application of ORC and/or OC to a target tissue could have clinical significance in managing pathologies which are not localized in a single specific location. This approach could also be leveraged for targeting therapies to particular structures such as arteries, lymphatics, and veins, which may be clinically relevant to the underlying pathology.

"Oxidized Regenerated cellulose (ORC) and/or Oxidized cellulose (OC)" is meant to include materials/products/articles/compositions/formulations comprising Oxidized Regenerated Cellulose (ORC)/OC, e.g. a biodegradable dressing, fibrin glue, synthetic glue, pads, matrices, powder, tabs, pills, sutures, fibers, dressings, stents, implants, scaffolds, solutions, gel, wax, gelatin, etc. all based on and/or comprising ORC/OC material. The ORC/OC can be in powder, beads, granules, agglomerates, woven, non-woven, knit, milled fibers, fine fibers, all either independently used or dispersed in a suitable medicament vehicle or in other forms. ORC/OC material can be used as a pad or powder, or can be part of another material.

In one embodiment, the ORC and/or OC is included in a device/article and/or as a coating on a device/article; such as implant, pacemaker, drain, artificial knee, etc. An article including the ORC and/or OC can be used in surgery to assist with the targeting of the glycolytic dependent therapy to the article and surrounding tissue. The ORC and/or OC coating can fully or partially cover the article.

The ORC and/or OC comprising/based material can be a dressing that utilize a fabric as a substrate, where the fabric substrate comprises fibers prepared from a biocompatible polymer(s), comprises a surface that possesses properties suitable for use as a hemostat, e.g. strength, flexibility and porosity. In certain embodiments of the invention, the ORC and/or OC may further include a hemostatic agent, or other biological or therapeutic compounds, moieties or species, including drugs and pharmaceutical agents. The agents may be bound within the fabric surfaces and/or within the fabric. The agents may be bound by chemical or physical means and are able to migrate from the dressing e.g. upon contact with blood in the body. The agent may be dispersed partially or homogenously through the fabric and/or the polymeric matrix. In some embodiments of the invention, the hemostatic agents, or other biological or therapeutic compounds, moieties or species, e.g. drugs, and pharmaceutical agents, may be "acid-sensitive", meaning that they may be degraded or denatured, or otherwise detrimentally affected, by acidic pH, such as is provided by conventional carboxylic-oxidized dressings.

The fabric substrates may be woven or nonwoven and may possess the physical properties necessary for use in hemostatic wound dressings. In one embodiment, a woven fabric has a dense, knitted structure that provides form and shape suitable for a hemostatic wound dressing. Such exemplary fabrics are described in U.S. Pat. No. 4,626,253, the content of which is hereby incorporated by reference herein as if set forth in its entirety.

In one embodiment of the present invention, the fabrics are warp knitted tricot fabrics constructed of bright rayon yarn which is subsequently oxidized to include carboxyl or aldehyde moieties in amounts effective to provide the fabrics with biodegradability and anti-microbial activity. In one embodiment, the fabrics are characterized by having a single ply thickness of at least about 0.5 mm, a density of at least about 0.03 g/cm$^2$, air porosity of less than about 150 cm$^3$/sec/cm$^2$, and liquid absorption capacity of at least about 3 times the dry weight of the fabric and at least about 0.1 g water per cm$^2$ of the fabric.

In one embodiment, the knitted fabrics have good bulk without undue weight, are soft and drapable, and conform well to the configuration of the surface to which they are applied. The fabric may be cut into suitable sizes and shapes without running or fraying along the cut edge. In one embodiment, fabric strength after oxidation is adequate for use as a surgical hemostat.

Fabrics that can be used according to the present invention comprise oxidized cellulose and are best characterized by their physical properties of thickness, bulk, porosity and liquid absorption capacity, as recited above. Suitable fabrics having these properties may be constructed by knitting 60 denier, 18-filament bright rayon yarn on a 32-gauge machine at a knit quality of 12. In one embodiment, a suitable tricot fabric construction is front-bar 1-0, 10-11; back-bar 2-3, 1-0. The extended shog movement imparted to the front bar may result in a 188 inch runner compared to a 70 inch runner for the back guide bar, and increases the fabric bulk and density. The ratio of front to back bar runners in this particular construction is 1:2.7.

The tricot fabrics that may be utilized in the present invention may be constructed from bright rayon yarns of from about 40 to 80 total denier. Each yarn may contain from 10 to 25 individual filaments, although each individual filament may be less than 5 denier to avoid extended absorption times. In one embodiment, the high bulk and fabric density are obtained by knitting at 28 gauge or finer, preferably at 32 gauge, with a fabric quality of about 10 or 12 (40 to 48 courses per inch). A long guide bar shog movement of at least 6 needle spaces, and preferably 8 to 12 spaces, may further increase fabric thickness and density.

Other warp knit tricot fabric constructions which produce equivalent physical properties may, of course, be utilized in the manufacture of the fabrics and dressings, and such constructions will be apparent to those skilled in the art. Polymers useful in preparing the fabric substrates in the dressing include, without limitation, collagen, calcium alginate, chitin, polyester, polypropylene, polysaccharides, polyacrylic acids, polymethacrylic acids, polyamines, polyimines, polyamides, polyesters, polyethers, polynucleotides, polynucleic acids, polypeptides, proteins, poly (alkylene oxide), polyalkylenes, polythioesters, polythioethers, polyvinyls, polymers comprising lipids, and mixtures thereof. Preferred fibers comprise oxidized regenerated polysaccharides, in particular oxidized regenerated cellulose. In one embodiment, oxidized polysaccharides are used to prepare a dressing to be used according to the invention. More preferably, oxizided cellulose is used to prepare the fabrics used in the dressing. The cellulose either may be carboxylic-oxidized cellulose, or may be aldehyde-oxidized cellulose. Even more preferably, oxidized regenerated cellulose is used to prepare fabric substrates used in the dressing. Typically, regenerated cellulose is preferred due to its higher degree of uniformity versus cellulose that has not been regenerated. Regenerated cellulose and a detailed description of how to make regenerated oxidized cellulose is set forth in U.S. Pat. Nos. 3,364,200 and 5,180,398, the content each of which is hereby incorporated by reference as if set forth in its entirety. As such, teachings concerning regenerated oxidized cellulose and methods of making same are well within the knowledge of one skilled in the art of such dressings.

Besides ORC, components such as non-regenerated oxidized cellulose (OC) may be considered for use with the cytotoxic glycolytic dependent compound. In one embodiment, cellulose in non-oxidazed form which does not have any carboxylic groups is not used.

Oxidized cellulose is a water-insoluble derivative of cellulose. It can be produced from cellulose by the action of an oxidizing agent, such as chlorine, hydrogen peroxide, peracetic acid, chlorine dioxide, nitrogen dioxide, persulfates, permanganate, dichromate-sulfuric acid, hypochlorous acid, hypohalites or periodates and a variety of metal catalysts. Oxidized cellulose may contain carboxylic acid, aldehyde, and/or ketone groups, in addition to the original hydroxyl groups of the starting material, cellulose, depending on the nature of the oxidant and reaction conditions. OC is typically an antihemorrhagic.

The dressing may utilize fabric substrates that have been oxidized to contain carboxyl moieties in amounts effective to provide the fabrics with biodegradability and anti-microbial activity. U.S. Pat. No. 3,364,200 discloses the preparation of carboxylic-oxidized cellulose with an oxidizing agent such as dinitrogen tetroxide in a Freon medium. U.S. Pat. No. 5,180,398 discloses the preparation of carboxylic-oxidized cellulose with an oxidizing agent such as nitrogen dioxide in a per-fluorocarbon solvent. After oxidation by either method, the fabric may be thoroughly washed with a solvent such as carbon tetrachloride, followed by aqueous solution of 50 percent isopropyl alcohol (IPA), and finally with 99% IPA. Prior to oxidation, the fabric can be constructed in the desired woven or nonwoven construct e.g. suitable for use as a hemostat. Certain dressings that utilize such fabrics have been found to provide and maintain hemostasis in cases of severe bleeding.

Typically, dressings that are compatible with acid-sensitive species comprise fabric substrates prepared from a biocompatible, aldehyde-oxidized polysaccharide. In such dressings, the polysaccharide preferably will contain an amount of aldehyde moieties effective to render the modified polysaccharide biodegradable, meaning that the polysaccharide is degradable by the body into components that are either resorbable by the body, or that can be passed readily by the body. More particularly, the biodegraded components do not elicit permanent chronic foreign body reaction when they are absorbed by the body, such that substantially no permanent trace or residual of the component is retained at the implantation site.

Aldehyde-oxidized polysaccharides may include, without limitation, cellulose, cellulose derivatives, e.g. alkyl cellulose, for instance methyl cellulose, hydroxyalkyl cellulose, alkylhydroxyalkyl cellulose, cellulose sulfate, salts of carboxymethyl cellulose, carboxymethyl cellulose and carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, heparin, heparin sulfate, heparan, heparan sulfate, dermatan sulfate, keratin sulfate, carrageenans, chitosan, starch, amylose, amylopectin, poly-N-glucosamine, polymannuronic acid, polyglucuronic acid, polyguluronic acid and derivatives of the above, each of which has been oxidized to included anti-microbial effective amounts of aldehyde moieties.

In some embodiments, when utilizing aldehyde-oxidized polysaccharides, the polysaccharide is oxidized to assure that the aldehyde-oxidized polysaccharide is biodegradable. Such biodegradable, aldehyde-oxidized polysaccharides may be represented by a Structure I in U.S. Pat. No. 8,709,463. In certain embodiments of the present invention, the biocompatible, biodegradable dressing comprises a fabric substrate prepared from a biocompatible, biodegradable, aldehyde-oxidized regenerated cellulose. In some embodiment, the aldehyde-oxidized regenerated cellulose is one comprising repeating units of Structure II in U.S. Pat. No. 8,709,463.

The dressing can be cut into different sizes and shapes to fit the surgical needs. It can be rolled up or packed into irregular anatomic areas. The fabric e.g. a knitted carboxylic-oxidized regenerated cellulose may be capable of providing and maintaining hemostasis in cases of severe bleeding.

In certain embodiments of the invention, a biologic, a drug, a hemostatic agent, a pharmaceutical agent, or combinations thereof, may be incorporated into the dressing.

To fabricate such a dressing, a drug or agent may be dissolved in an appropriate solvent. The fabric may then be coated with the drug solution and the solvent removed. Preferred biologics, drugs and agent include analgesics, anti-infective agents, antibiotics, adhesion preventive agents, pro-coagulants, and wound healing growth factors.

In some embodiments of the invention, the aldehyde-oxidized regenerated polysaccharide, e.g. cellulose, is essentially free of functional or reactive moieties other than aldehyde moieties. By essentially free, it is meant that the polysaccharide does not contain such functional or reactive moieties in amounts effective to alter the properties of the aldehyde-oxidized polysaccharide, or to provide the fabric comprising the polysaccharide with a pH of less than about 4.5, more preferably less than about 5, or greater than about 9, preferably about 9.5. Such moieties include, without limitation, carboxylic acid moieties typically present in wound dressings made from carboxyl-oxidized cellulose. Excess levels of carboxylic acid moieties will lower the pH of the fabrics and dressings so that they are not compatible for use with those acid-sensitive species that may be degraded or denatured by such a low pH, e.g. thrombin. Other moieties essentially excluded include, without limitation, sulfonyl or phosphonyl moieties.

Hemostatic agents that may be used in the dressing include, without limitation, procoagulant enzymes, proteins and peptides, can be naturally occurring, recombinant, or synthetic, and may be selected from the group consisting of prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin and vasopressin analogs, epinephrine, selectin, procoagulant venom, plasminogen activator inhibitor, platelet activating agents, synthetic peptides having hemostatic activity, derivatives of the above and any combination thereof. Preferred hemostatic agents used in the present invention are thrombin, fibrinogen and fibrin.

Protein-based hemostatic agents, such as thrombin, fibrin or fibrinogen, if bound to the dressing, can enhance the hemostatic property of aldehyde-oxidized regenerated cellulose dressing and reduce the risk of thrombosis caused by free hemostatic agents migrating into the blood stream. Hemostatic agents may be bound to the dressings either by chemical of physical means. Agents may be covalently conjugated with aldehyde groups pendant from the polysaccharide in one instance, thus chemically binding the agent to the wound dressing. The hemostatic agents can be physically bound to the dressing via incorporation into the polymeric matrix dispersed on and through the aldehyde-oxidized polysaccharide fabric and immobilized, i.e. bound, via lyophilization.

The features of such hemostatic agents conjugated with the aldehyde-oxidized regenerated cellulose dressing can be controlled to suit a desired application by choosing the conditions to form the composite hemostat during conjugation.

In such cases, aldehyde-oxidized regenerated cellulose fabric may be immersed in the solution of thrombin, fibrinogen or fibrin to provide homogeneous distribution throughout the wound dressing.

The aldehyde-oxidized regenerated cellulose fabric can be soaked with the desired amount of aqueous solution of thrombin, then reacted with aqueous solution of sodium borohydride or sodium cyanoborohydride reconstituted in phosphate buffer (PH=8).

In certain embodiments of the invention, the ORC and/or OC do not include a blood coagulation factor protein and/or enzyme.

One skilled in the art, once having the benefit of this disclosure, will be able to select the appropriate hemostatic agent, depending on the particular circumstances and properties required of the particular dressing.

Some ORC materials has the advantage of decreasing adhesions at the surgical site e.g. as INTERCEED® (TC7) Absorbable Adhesion Barrier. ORC can be part of a composite dressing such as the commercially available dressing EVARREST® Fibrin Sealant Patch.

A dressing based on and/or comprising ORC can be an absorbable textile such as a knitted, woven, non-woven or loose fibers prepared by the controlled oxidation of regenerated cellulose. ORC granules and/or fine fibers can vary in bulk density to as low as 0.10 g/cc and up to as high as 0.85 g/cc (dependent on micron size or micron particle size). These granules and/or fine fibers can be tableted/granulated into denser shapes and structures/forms, which could be incorporated into other materials e.g. for controlled release.

In one embodiment, the ORC or OC can be altered to modify their chemoattractant properties for glycolytic dependent compounds and/or to control ORC degradable properties i.e. absorption time. For example, ORC modifications may include alterations in carboxylation or oxidation levels. Typically, oxidation level is measured by the amount of carboxyl content. The carboxylation level in ORC may range from about 0.10% to 99.99% per USP (United States pharmacopeia). The oxidation level in ORC may range from about 0.10% to 99.99% per USP.

In one embodiment, the carboxylation level in ORC is in the range of about 6% to 25.5% per USP. In one embodiment, a suitable ORC carboxylation level is in the range of 12-18% per USP resulting in an ORC absorption time of 10 days to 8 weeks. In one embodiment, a suitable ORC carboxylation level is in the range of 18-21% per USP resulting in an ORC absorption time of 7-14 days. In one embodiment, a suitable ORC oxidation level is in the range of 12-18% per USP resulting in an ORC absorption time of 10 days to 8 weeks. In one embodiment, a suitable ORC oxidation level is in the range of 18-21% per USP resulting in an ORC absorption time of 7-14 days.

In one embodiment, the carboxylation level is in the range of about 18-21% per USP e.g. as in the commercially available SURGICEL® absorbable hemostat which is composed of oxidized regenerated cellulose. In another embodiment, the carboxylation level is 12-18% per USP e.g. as in the commercially available INTERCEED® (TC7) Absorbable Adhesion Barrier. In the case that a dressing comprising ORC material is used, the textile density may be from about 50-250 g/m$^2$. In one embodiment, the textile density is in the range of about 45 to 80 gm/m$^2$, in the range of 45-75 gm/m$^2$, 55-75 gm/m$^2$, or in the range of 60-80 gm/m$^2$ e.g. as in the commercially available SURGICEL® absorbable hemostat which is composed of oxidized regenerated cellulose. In another embodiment, the textile density is in the range of as low as 0.10 g/m$^2$ and up to as high as 250 g/m$^2$ e.g. as in the commercially available SURGICEL NU-KNIT® absorbable hemostat and INTERCEED® (TC7) Absorbable Adhesion Barrier which are both composed of 100% oxidized regenerated cellulose.

In another embodiment, the particle/fiber density is in the range of as low as 0.10 g/m$^2$ and up to as high as 0.85 g/m$^2$ (dependent on micron size or micron particle size) e.g. as in the commercially available INTERCEED® (TC7) Absorbable Adhesion Barrier which is composed of oxidized regenerated cellulose.

Physical attributes (e.g. porosity, impaction/density, shape, etc.) of the ORC materials can be varied to achieve a desired absorption time. Absorption times can be associated with carboxylation or oxidation level, material density, and availability of surface area. Furthermore, the tissue site, surgical location, patient dependent factors (such as immunological status) and/or cellular pathology can alter the absorption time. In one embodiment, the absorption time is in the range of approximately 1-30 days e.g. 6-14 days as in the commercially available SURGICEL® absorbable hemostat which is composed of oxidized regenerated cellulose. In another embodiment, the absorption time is 10 days and up to 8 weeks e.g. e.g. as in the commercially available INTERCEED® (TC7) Absorbable Adhesion Barrier which is composed of oxidized regenerated cellulose.

According to the invention, ORC and/or OC pouches can be wrapped around target tissues, ORC and/or OC can be delivered to the target tissues by laparoscopic tools to minimize target tissue disruption, the ORC and/or OC material can be conformed to the topography of a solid organ.

The ORC and/or OC can be delivered to the treatment site (e.g. to the pathological cells and/or a surgical site following tumor resection) by using ligands to the targeted site. The targeting species include antibodies as well as other peptides with specific affinity to the targeted cell.

In one embodiment, the method comprises administering, e.g. adjacent or in direct connection with the malignant cell, a multilayered wound dressing comprising a first absorbable nonwoven fabric; a second absorbable woven or knitted fabric comprising ORC; and optionally thrombin and/or fibrinogen. Examples of ORC compositions are as disclosed in WO2006044882 and WO2006044879, both incorporated herein in their entirety by reference. Non limiting examples of commercially available dressings made/based on Oxidized Regenerated Cellulose are SURGICEL® absorbable hemostat; SURGICEL NU-KNIT® absorbable hemostat; SURGICEL FIBRILLAR® absorbable hemostat; SURGICEL SNOW® Absorbable Hemostat; INTERCEED® (TC7) Absorbable Adhesion Barrier; EVARREST® Fibrin Sealant Patch; OXYCEL® absorbable cellulose surgical dressing.

An exemplary description of how to make ORC is set forth in U.S. Pat. Nos. 3,364,200, 5,180,398 and 4,626,253, the contents of which is hereby incorporated by reference as is set forth in its entirety.

Interestingly, it was reported that a dressing composed of Oxidized Regenerated Cellulose [ORC; fibrillar cellulose (SURGICEL®)] used after resection of malignant cells (due to persistent bleeding in the tissues) falsely indicated cancer recurrence when tested using Computed Tomography (CT) and/or Positron Emission Tomography (PET) imaging following 18FG administration. PET/CT identified an intense localization of 18FG in the region of the dressing. In the reports it was concluded that currently, a second examination may be necessary to settle the true nature of the findings in such cases (see Fournet S. et al. "False positive lymph node activity on positron emission tomography (PET/CT) due to hemostatic compresses". J Visc Surg. 2011 April; 148(2):e153-5; Wang H and Chen P. "SURGICEL® (oxidized regenerated cellulose) granuloma mimicking local recurrent gastrointestinal stromal tumor: A case report". Oncol Lett. 2013 May; 5(5):1497-1500).

This phenomenon is probably as a result of accumulation of 18FG nearby the ORC and/or at the ORC application place. In some cases the ORC was still intact. However, in other cases the ORC had recently been absorbed such that even though ORC was at least partially absorbed, the 18FG was localized. In the latter case, it may be that the 18FG was absorbed by the tissues that were using the largest amount of glucose.

At this moment, this accumulation of 18FG nearby ORC and/or at the ORC application place is inconvenient to surgical and radiological teams, which must be careful not to confuse the cancer like image with cancer recurrence. This accumulation is a false positive artifact. The Applicant's invention makes a beneficial use of 18FG accumulation nearby and/or at the ORC application place. For example, placement of ORC in proximity and/or in direct connection with a pathological cell e.g. malignant cell will result in selective localization of a cytotoxic glycolytic dependent compound nearby the pathological cell as compared to the localization nearby cells that were relatively distant from the ORC application place. In another embodiment, placement of ORC in proximity and/or in direct connection with a pathological cell e.g. malignant cell will result in selective uptake or internalization of a cytotoxic glycolytic dependent compound into the pathological cell as compared to the internalization into cells that were relatively distant from the ORC application place.

Typically, uptake of cytotoxic glycolytic dependent compounds through intracellular transporters is directly proportional to the glycolytic activity of the cells. In some embodiments, a variation in the glycolytic activity of cells/tissues/organs by using ORC will proportionately affect the uptake of the cytotoxic glycolytic dependent compound. Improving the cellular specificity of therapeutic compounds may limit the complications of non-pathologic tissues coming in contact with cytotoxic therapies.

A desired time for administration of the cytotoxic glycolytic dependent compound may be a time resulting in reaching a certain or maximal level of GLUT receptors on the diseased cell/tissue/organ after ORC exposure. The desired time can be monitored periodically by constantly testing accumulation level of FG18 in the diseased cell/tissue/organ after ORC exposure and e.g. finding the time in which the accumulation of receptors is maximal.

Targeting pathological cells such as cancerous cells may be further complicated by the tolerance of such cells to particular treatments. Cancerous cells may in many cases be unresponsive to certain therapies through cellular adaptation. Without being bound by the mechanism, it is possible that artificial stimulation of tissue glucose transporters, using ORC based materials, may prevent pathologies from achieving resistance to particular therapies. Also, ORC may produce an increase in glucose standard uptake values, such that therapies that depend on these pathways overcome cellular adaptation. Without being bound by the mechanism, it is likely that the glycolytic effect may be enhanced in tissue adjacent to ORC as long as the glycolytic effect caused by ORC is present.

In one embodiment, ORC is placed at a site (e.g. a surgical site) wherein localization of a cytotoxic glycolytic dependent compound is desired e.g. a cancer site. In one embodiment, a combination treatment of ORC and a cytotoxic glycolytic dependent compound will improve the selective absorption and intracellular delivery of the cytotoxic glycolytic compound to pathological cells. In one embodiment, the cytotoxic glycolytic dependent compound is given in combination with ORC to target the cytotoxic glycolytic dependent compound to the tissues intended to be treated, as long as they are not in a blended form. Advantageously, the approach of leveraging the known pharmacologic pathways of glycolytic dependent compounds will create new therapeutic options for the patient and their healthcare providers in targeting glycolytic compounds to specific cells, tissues, organs etc.

In one embodiment, the combination methods increase the glycolytic activity of the targeted cell with placement of ORC and/or OC (e.g. by an increase in glucose transporters) and in turn the delivery and/or effect of cytotoxic compounds, that are dependent on glucose transport, to the cell increases. In one embodiment, ORC and/or OC stimulates the activity of GLUTs present in tissue. In one embodiment, increased activity of GLUTs, secondary to ORC and/or OC application, proportionately enhances the effect of glycolytic dependent therapies which rely on GLUTs for their cellular transport.

In one embodiment, the therapeutically effective dose of the cytotoxic glycolytic dependent compound is lower than a standard dose administered in the absence of ORC and/or OC. In another embodiment, the combination treatment allows for a shorter treatment period as compared to the current/standard therapy that is separate or not used in combination with ORC and/or OC. In such embodiments, the improved selectively of a cytotoxic glycolytic dependent compound towards a targeted cell will lower the systemic exposure and/or absorption of the compound to non-pathological cells and thus lower or eliminate the complications/side effects associated with the exposure of non-pathological cells to the cytotoxic glycolytic dependent compound.

The term "therapeutically effective dose" refers to a dose required to reduce and/or eliminate pathological cells e.g. a dose required to reduce the size of a tumor mass. The effective amount can be measured based on any change in the course of the disease in response to the administration of the compound. The effective dose can depend on the route of administration, the phase of the disease (e.g. early or advanced) and other factors which can be recognized by the skilled artisan e.g. depending on the therapy, condition being treated, patient characteristics, administration of several glycolytic dependent compounds administered in parallel and/or one after the other; and/or administration of other medications or treatments (e.g. radiation) together with a glycolytic dependent compound(s). In one embodiment, the therapeutically effective dose of the cytotoxic glycolytic dependent compound in the combination treatment is lower than a standard dose administered in the absence of ORC and/or OC e.g. when administered in the same administration route. The term "standard dose" relates to the currently effective dosage therapy of a particular type of glycolytic depended compound when administered separately or not in combination with ORC and/or OC; or e.g. relates to a current effective dosage therapy of a particular type of glycolytic depended compound, in a responsive patient, when ORC and/or OC is not administered to the patient.

In certain embodiments a "therapeutically effective dose" is measured by calculating the range between the minimum effective dose (MED) and the maximum tolerated dose (MTD). These values could be established from known literature according to each therapeutic.

In certain embodiments a "therapeutically effective dose" refers to the median effective dose ED50, for a particular know drug. For example, Doxorubicin has a biological half-life of: Triphasic; 12 minutes, 3.3 hours, 30 hours. Mean: 1-3 hours. Typically, 5 times the elimination half-life will give the time at which point the drug has been completely eliminated from the body. For Doxorubicin this would be 5-15 hours.

In another embodiment, in the presence of ORC and/or OC, the compound is administered for a shorter period of time as compared to the time period in the standard therapy used in the absence of ORC and/or OC. The term "standard therapy" particularly relates to the current period of time that a particular type of glycolytic dependent compound is administered and/or to the number of cycles that the compound is administered to the patient not in combination with ORC and/or OC. Standard therapy time e.g. relates to a current period of time that a particular type of glycolytic depended compound is used in a responsive patient when ORC and/or OC is not administered to the patient.

The combination treatment according to the invention (e.g. including administration of ORC and/or OC and a cytotoxic glycolytic dependent compound) may include other medications, treatments and/or other glycolytic dependent compounds as the standard therapy.

The standard doses and standard therapies can be determined, in part, by practices e.g. as detailed for several glycolytic depended compounds in Table 1 herein. Also, the standard doses and the standard therapies can be as detailed in: Martindale. The Complete Drug Reference Thirty-sixth edition Edited by Sean C Sweetman BPharm, FRPharmS (incorporated herein by reference).

Below are examples of several "standard doses" and "standard therapies" for cytotoxic glycolytic dependent compounds:

Doxorubicin 60 mg/m$^2$ IV day 1 and cyclophosphamide 600 mg/m$^2$ IV day 1. 21 days (for 4 cycles; some studies used up to 8 cycles). Breast cancer.

Doxorubicin 60 mg/m$^2$ IV day 1 and paclitaxel 200 mg/m$^2$ IV day 1. 21 days (for 4 cycles). Breast cancer.

Doxorubicin 50 mg/m$^2$ IV day 1 and docetaxel 75 mg/m$^2$ IV day 1. 21 days (for up to 8 cycles). Breast cancer (metastatic).

Cyclophosphamide 750 mg/m$^2$ IV day 1; doxorubicin 50 mg/m$^2$ IV day 1; and prednisone 40 mg/m$^2$ oral days 1-5. 28 days. Chronic lymphocytic leukaemia.

Cyclophosphamide 500 mg/m$^2$ IV day 1; doxorubicin 50 mg/m$^2$ IV day 1; and cisplatin 50 mg/m$^2$ IV day 1 (these doses are optimised from the original 600 mg/m$^2$, 45 mg/m$^2$, and 50 mg/m$^2$ respectively). 21 days (for 6 cycles). Ovarian cancer.

Etoposide 120 mg/m² IV days 4-6; doxorubicin 20 mg/m² IV days 1, 7; and cisplatin 40 mg/m² IV days 2, 8. 21-28 days. Stomach cancer.

Epirubicin 50 mg/m² IV day 1; cisplatin 60 mg/m² IV day 1; and fluorouracil 200 mg/m² daily continuous IV. 21 days (for up to 8 cycles). Stomach cancer.

Fluorouracil 600 mg/m² IV days 1, 8, 29, 36; doxorubicin 30 mg/m² IV days 1, 29; and mitomycin 10 mg/m² IV day 1. 56 days. Stomach cancer, pancreatic cancer.

Paclitaxel 135 mg/m² continuous IV over 24 hrs, day 1 and cisplatin 75 mg/m² IV day 1. 21 days (for 6 cycles). Ovarian cancer.

Accordingly, in one embodiment, the combination treatment allows for lower doses and/or shorter period of times than those elaborated in Table 1 and/or those elaborated in Martindale.

It is also possible to use the "standard doses" and "standard therapies" of cytotoxic glycolytic dependent compounds to achieve a greater therapeutically effect. With greater targeting of glycolytic dependent therapies the patient may be able to receive the same dose, as standard medical regimens, but have greater clinical response; secondary to the enhanced targeting of the therapy.

In view of the selectivity of the method the patient may be able to support the same therapy dose or higher with minimal or no side effects. E.g. it is well known that the number of normal leukocytes and/or platelets decrease following chemotherapy. A more selective treatment may overcome this unwanted side effect.

Additionally, with greater targeting of glycolytic dependent therapies the patient may be able to receive a lower, as standard medical regimens, but have greater clinical response; secondary to the enhanced targeting of the therapy. Increased targeting may also allow for shorter treatment duration, secondary to the enhanced targeting of the therapies.

The combined treatment of ORC and/or OC and the cytotoxic glycolytic dependent compound may also be advantageous in destroying pathological cells having a limited/low glycolytic metabolism e.g. a malignant cell that replicates relatively slowly. Accordingly, without being bound by the mechanism, ORC and/or OC may act as a chemoattractant agent for glycolytic dependent therapies.

Typically, the BBB is a physiologic obstruction to the delivery of systemic therapy to the brain parenchyma and CNS. In one embodiment, the combination treatment is used to enhance the penetration of a cytotoxic glycolytic dependent compound through the blood-brain barrier (BBB) e.g. to treat primary and metastatic disease found within the central nervous system (CNS). Typically, cells in the BBB are capable of transporting metabolic molecules, like glucose, using glucose transporters present in the BBB. In one embodiment, ORC and/or OC in proximity to the BBB increases the localization, targeting and/or uptake of glycolytic dependent therapies across the BBB.

In one embodiment, the combination treatment is used to augment/improve the targeting of cytotoxic glycolytic dependent compounds to diseased/pathologic cells that have poor glycolytic properties, tissues that necessitate large quantities of glycolytic dependent compounds and/or in glycolytic dependent compounds that have high cytotoxicity profiles in clinically effective doses which limit their clinical applications.

In another embodiment, the combination treatment offers the potential to stimulate absorption of glycolytic therapies into cells/tissues/organs that are not using glucose transporters. In such an embodiment, it is conceivable that artificial stimulation of cells glycolytic state could serve as a method of concentrating glycolytic dependent therapy in metabolically limited/varied/dormant/transient cells/tissues/organs. This in essence could cause larger quantities to glycolytic therapies to be absorbed in cells even as their own metabolic processes are shutting down.

In one embodiment, the method is used in the field of Surgical and Hematologic oncology. In one embodiment, the method is used in operable and non-operable cancer patients. Typically, operable tumors are cancers that can be removed completely or partially by a surgical procedure. Inoperable tumors are those located in an inaccessible area e.g. in the brain, or tumors that are composed of multiple tumors that cannot be completely removed or in patients having cancer in an advanced stage. In one embodiment, the methods according to the invention are used to deliver a cytotoxic glycolytic dependent compound to a surgical site following partial or complete tumor resection. In such an embodiment, the therapeutically effective dose of the cytotoxic glycolytic dependent compound is lower than a standard dose administered in the absence of ORC and/or OC and/or allows for a shorter treatment period as compared to the current therapy that is separate or not used in combination with ORC and/or OC, or allows for response in a patient that is not responsive. In one embodiment, the method is used in a bleeding site. In another embodiment, the method is used in a non-bleeding site. In another embodiment, the method is used at a site wherein tumor resection was not carried out or in the absence of tumor resection.

In one embodiment ORC and/or OC will be administered in a non-bleeding site and/or in the absence of tumor resection.

In one embodiment, coordinating ORC and/or OC breakdown/absorption times with a scheduled regimen of a cytotoxic glycolytic dependent compound allows for precise delivery of a cytotoxic glycolytic dependent compound to a pathological cell over a predetermined period of time. For example, ORC and/or OC oxidation/carboxylation rates will alter the absorption of the ORC and/or OC material in tissue beds.

Typically, carboxylation or oxidation level will alter the rate of absorption such that a higher carboxylation or oxidation will be faster absorbed whereas a lower carboxylation or oxidation is absorbed slower. Other physical aspects, such as ORC and/or OC density and available surface area will proportionality elongate or shorten the absorption time, secondary to material mass all as described above. Typically, the higher the mass of the ORC and/or OC material, a longer absorption time will be achieved. Additionally, a high mass ORC and/or OC with low surface area will also take longer to be resorbed by the body.

As used herein, the indefinite articles "a" and "an" mean "at least one" or "one or more" unless the context clearly dictates otherwise.

The following examples are illustrative but not limiting.

EXAMPLES

Primary Breast Cancer Disease.
Stage III Breast Cancer:
In stage III breast cancer, the tumor is greater than 5 cm, or growing into adjacent tissues, or the cancer has spread to local lymph nodes. These cancers are managed with chemotherapy before surgery (neoadjuvant chemo). Shrinking the tumor preoperatively may allow for breast conserving surgery (BCS). However, in some cases a mastectomy is done. For stage III cancers, axillary lymph node dissection is done to look for spread of disease.

Another option for stage III cancers is to treat with surgery first. Because these tumors are fairly large and/or have grown into nearby tissues, this usually means a mastectomy. In these cases, surgery is followed by adjuvant systemic chemotherapy, and/or hormone therapy, and/or trastuzumab. Radiation is recommended after surgery.

After surgery (adjuvant chemotherapy): When therapy is given to patients with no evidence of cancer after surgery, it is called adjuvant therapy. Surgery is used to remove all of the cancer that can be seen, but adjuvant therapy is used to kill any cancer cells that may have been left behind or spread but can't be found. Untreated, these cells can establish new tumors in other places in the body. Adjuvant therapy after breast-conserving surgery or mastectomy reduces the risk of breast cancer recurrence.

Side effects: Some women develop heart damage during or after treatment with the antibody drugs (trastuzumab, pertuzumab, and ado-trastuzumab emtansine). This can lead to a problem called congestive heart failure. For many patients this effect lasts a short time and gets better when the drug is stopped. The risk of heart problems is higher if these drugs are given with certain chemo drugs that also can cause heart damage, such as doxorubicin (Adriamycin) and epirubicin (Ellence).

In most cases (especially adjuvant and neoadjuvant treatment), chemotherapy is most effective when given in combinations of more than one drug. Multiple combinations are used, and it is not clear that any single combination is clearly the best.

The most common chemo drugs used for early breast cancer include the anthracyclines (such as DOXORUBICIN/ADRIAMYCIN® and EPIRUBICIN/ELLENCE®) and the taxanes (such as PACLITAXEL/TAXOL® and DOCETAXEL/TAXOTERE®). These may be used in combination with certain other drugs, like fluorouracil (5-FU), cyclophosphamide (CYTOXAN®), and carboplatin.

Information is obtained from the American Cancer Society.

The following is the currently used postoperative systemic cytotoxic chemotherapy with DOXIL® (Doxorubicin): a dose of 60 mg/m$^2$ is administered daily IV for 3 days, or 30-60 mg/m$^2$ IV weekly.

Ovarian Cancer Disease.

In the majority of patients, ovarian cancer remains occult and becomes symptomatic after it has already metastasized to the peritoneal cavity. During this clinical stage ovarian cancer typically presents with malignant ascites. It is important to accurately stage this cancer with laparoscopy, ultrasound, and CT scanning. Patients with stage I disease benefit from whole-abdomen radiotherapy and may receive additional benefit from combination chemotherapy e.g. glycolytic dependent therapy—cisplatin together with an alkylating agent—cyclophosphamide. Such combination chemotherapy is also a standard approach to stage III and stage IV disease. Randomized clinical studies have shown that the combination of paclitaxel and cisplatin provides survival benefit compared with the previous standard combination of cisplatin plus cyclophosphamide (an alkylating agent). More recently, several studies have shown that carboplatin and paclitaxel yields clinical results similar to what is achieved with cisplatin plus paclitaxel combination; however, because of reduced toxicity and greater ease of administration, carboplatin plus paclitaxel has now become the treatment of choice. In patients who present with recurrent disease, the topoisomerase I inhibitor topotecan, the alkylating agent altretamine, and liposomal doxorubicin are used as single agent monotherapy (Katzung, Bertram G. Basic & Clinical Pharmacology 9TH Edition McGraw-Hill Medical McGraw-Hill Medical. New York 2006. Section 9e, page 48).

The following is the currently used postoperative systemic cytotoxic chemotherapy with DOXIL® (Doxorubicin) for patients with Ovarian Cancer:

DOXIL (Doxorubicin Hcl Liposome Injection) is administered intravenously (IV) at a dose of 50 mg/m$^2$ once a month. A minimum of 4 courses is recommended. An initial rate of 1 mg/min is used with the first dose of DOXIL®. If no infusion-related adverse reactions are observed, the rate is increased. The patient is administered with DOXIL® every 4 weeks for as long as the patient does not clinically progress, continues to tolerate treatment, and shows no evidence of cardiotoxicity. When Doxorubicin is used with other chemotherapy drugs e.g. Paclitaxel, Trastuzumab (HER2/neu receptor), cyclophosphamide (an alkylating agent), the most commonly used dosage of Doxorubicin is 40 to 60 mg/m$^2$ IV every 21 to 28 days. Alternatively, 60 to 75 mg/m$^2$ IV once every 21 days. The lower doses are recommended for patients with inadequate marrow reserves due to old age, prior therapy, or neoplastic marrow infiltration. According to the American Cancer Society, surgery is the main treatment for most ovarian cancers. For women of childbearing age with cancer is in the earliest stage, it may be possible to treat the disease without removing both ovaries and the uterus.

For epithelial ovarian cancer, surgery has 2 main goals: staging and debulking.

For other types of ovarian cancer (germ cell tumors and stromal tumors), the main goal of surgery is to remove the cancer.

Staging epithelial ovarian cancer—Surgery for ovarian cancer has 2 main goals. The first goal is to stage the cancer—to see how far the cancer has spread from the ovary. Usually this means removing the uterus (this operation is called a hysterectomy), along with both ovaries and fallopian tubes (this is called a bilateral salpingo-oophorectomy or BSO). In addition, the omentum is also removed (an omentectomy).

Some lymph nodes in the pelvis and abdomen are biopsied (taken out to see if the cancer has spread from the ovary). If there is fluid in the pelvis or abdominal cavity, it will also be removed for analysis.

Debulking epithelial ovarian cancer—Debulking is very important in any patient with ovarian cancer that has already spread throughout the abdomen. The aim of debulking surgery is to leave behind no tumors larger than 1 cm. This is called optimally debulked. Sometimes the surgeon will need to remove a piece of colon to debulk the cancer properly. Debulking may also require removing the spleen and/or the gallbladder, as well as part of the stomach, liver, and/or pancreas.

Chemotherapy (chemo) is the use of drugs to treat cancer. Most often, chemo is a systemic treatment—the drugs are given systemically and reach all areas of the body. Systemic chemo can be useful for cancers that have metastasized (spread). Most of the time, systemic chemo uses drugs that are injected into a vein (IV) or given by mouth Chemotherapy for epithelial ovarian cancer:

Chemo for ovarian cancer is most often a combination of 2 or more drugs, given IV every 3- to 4-weeks. Giving combinations of drugs rather than just one drug alone seems to be more effective in the initial treatment of ovarian cancer.

The standard approach is the combination of a platinum compound, such as cisplatin or carboplatin, and a taxane, such as paclitaxel (TAXOL®) or docetaxel (TAXOTERE®). For IV chemotherapy, most doctors favor carboplatin over cisplatin because it has fewer side effects and is just as effective.

The typical course of chemo for epithelial ovarian cancer involves 3 to 6 cycles. A cycle is a schedule of regular doses of a drug, followed by a rest period. Epithelial ovarian cancer often shrinks with chemo, but the cancer cells may eventually reoccur. Albumin bound paclitaxel (nab-paclitaxel, ABRAXANE®).

Additional chemotherapies for Ovarian Cancer Disease:
Altretamine (HEXALEN®)
Capecitabine (XELODA®)
Cyclophosphamide (CYTOXAN®)
Etoposide (VP-16)
Gemcitabine (GEMZAR®)
Ifosfamide (IFEX®)
Irinotecan (CPT-11, CAMPTOSAR®)
Liposomal doxorubicin (DOXIL®)
Melphalan
Pemetrexed (ALIMTA®)
Topotecan
Vinorelbine (NAVELBINE®)

Example 1

The Effect of ORC on Cancer Treatment with a Cytotoxic Glycolytic Dependent Compound To enhance the efficacy of a glycolytic dependent compound/chemotherapy in cancer treatment, in the following example a combination treatment of a cytotoxic glycolytic dependent compound and ORC is used to treat a patient with stage III breast cancer disease.

In these patients the surgeon performs a breast conserving surgery (BCS) or mastectomy, with sentinel lymph node biopsy with or without, axillary lymph node dissection. During the procedure, an ORC material/structure e.g. a pad, powder, or material, is used intraoperatively and left in the tumor bed (or site of tumor removal, site of metastatic concern, site of lymphatic drainage, etc.) before closing the surgical site. The surgeon approximates the ORC around the tumor bed while maintaining proper surgical technique. The approximation of ORC is carried out according to the form of ORC used. If a powder form ORC is used, the surgeon can cover the desired area. If the ORC is in the form of a pad, pill, suture, mesh, the surgeon may need to fix the ORC in place with an anchoring mechanism. An anchoring mechanism could be suture, staples, adhesive/sealant, or clips, commonly used to approximate tissue and medical devices, in current surgical practice. This will be site specific and at surgeon's discretion. The ORC material may also comprise fibrin sealant components in powder form that can be hydrated at the surgery site and/or prior to ORC placement at the desired site.

The amount or ORC will be dependent on the intraoperative and postoperative effect desired by the surgical team. Cancer size and anatomical location would likely affect the quantity and form of ORC placed. Furthermore, the surgical approach will impact how the surgical team will be able to access tissues and may limit placement of ORC. Accessory products could be optimized to assist in the placement of ORC in more challenging minimally invasive surgical approaches. For example, SURGICEL SNOW® Absorbable Hemostat is a structured non-woven form of ORC. This form of ORC allows it to be deployed and manipulated during minimally invasive procedures, such as those performed using laparoscopic approaches. Additionally, this form of ORC has enhanced conformability and handling characteristics, when compared to other forms of ORC.

Following ORC placement, the surgeon closes the fascial layers, leaving the ORC adjacent to the tumor bed/surgical site. The ORC remains in the tumor bed for the immediate postoperative period and slowly degrade over the following weeks/months. After locating the ORC adjacent to the tumor bed, the patient begins post-operative chemotherapy/glycolytic dependent therapy.

In view of the combination treatment of ORC and glycolytic therapeutics, the patient could receive lower doses and/or fewer cycles and have improved results as compared to treatment with Doxorubicin in the absence of an ORC-based product. The lower doses of glycolytic therapies are more tolerable and also advantageous for the elderly or patients with marrow infiltration. Alternatively, treatment with ORC will decrease the reduction in platelets/leukocytes after a chemotherapy cycle and allow completion of the multiple cycle treatment as scheduled and without disruption.

Beneficial treatment effects could be measured in a number of ways such as measuring the activity of Hepatic enzymes, Renal studies, serial CBCs, patient QOL (quality of life), 18FG uptake, Overall Survival, distant metastasis rates, local metastasis rates, along with other commonly used metrics for evaluating patients undergoing chemotherapy.

In another example, beneficial effect of ORC on normal cells after chemotherapy treatment of a patient is measured by measuring platelets/leukocytes levels.

In another example a combination treatment of a cytotoxic glycolytic dependent compound and ORC is used to treat a patient with ovarian cancer disease.

ORC can be applied at the site of ovarian cancer resection during the debulking procedure. ORC can be placed in proximity to the resected tissue bed, and left in place following the procedure. The surgical team can attempt to cover areas where the ovarian cancer is likely to reoccur and/or prone for spread with ORC. Following surgery, the placement of ORC intraoperatively will enhance the targeting of glycolytic dependent chemotherapies during the treatment period. The ORC can be placed during the closure and approximation of resected tissue sites.

Example 2

The Effect of ORC on Cancer Treatment with a Cytotoxic Glycolytic Dependent Compound in the Absence of Resection There are multiple situations where surgery cannot be conducted due to the location of the tumor, tumor type, patient comorbidities, and/or surgical capabilities. Inoperable tumors are managed using treatments and combinations of treatments, such as chemotherapy, radiation therapy, and other palliative treatments.

Clinically, there are cases when a brain tumor is inoperable, due to the location of the tumor. These cases could involve the placement of ORC in proximity of the tumor site, without resection of the tumor. The localization of the ORC in proximity to the nonresected tumor bed could enhance the localization of glycolytic therapies in these difficult clinical cases.

Materials and Methods for Example 3:
Abbreviation:
NHDF: Normal Human Dermal Fibroblast; FBM: Fibroblast Basal Medium; P/S: Penicillin Streptavidin; FBS: Fetal Bovine Serum; Dox: Doxorubicin hydrochloride, ORC: Oxidized Regenerated Cellulose; PuW: Pure Water; GM: Growth Medium.

Materials and Methods:
NHDF cells: Lonza, Cat #: CC2511; FBM: Lonza, Cat #: CC-3131; P/S: Biological industries, Cat #: 03-031-1B; FBS: Biological industries, Cat #04-121-1A; Trypsin/EDTA: Biological industries, Cat #: 03-054-1B; Dox: TCI, Cat #: D4193, Lot #: U43TK-OH; Nu-Knit Surgicel© (ORC): Ethicon, Cat #: A311012.013547; WST-1: Roche, Cat #: 11644807001.

Instruments:
Acu-Punch 8 mm: Acuderm inc. USA, Cat #: P825 for creating ORC circles of specific sizes.
Flask 175 cm$^2$: Corning, Cat #: 431080.
500 ml 0.22 μm Cellulose Acetate Filter, Corning, Cat #:430769.
24 well plate: Costar, Cat #: 3524.
37° C. Water-jacketed Incubator with 5% $CO_2$.

Preparation of Reagents:
Growth medium: 450 ml FBM, 50 ml FBS, 5 ml P/S filtered with 0.22 μm cellulose acetate filter. Stored up to 1 month at 2° C.-8° C.
Dox stock solution: 25 mg of Dox powder was dissolved in 2.5 ml sterile PuW for a 10 mg/ml solution (17.24 mM).
NU-KNIT® (ORC) patch: NU-KNIT® was cut with an 8 mm punch to form 8 mm circles of Nuknit. These circles were then cut into 4 quarters using sterile scissors (each quarter has a weight of 2.2-2.7 mg, Average 2.44 mg, n=10).

Assay Workflow for Example 3:
Day 1: Two 24-well plates were seeded with 15,000 NHDF cells/well using a 15,000 cells/ml suspension according to the plate layout below (representing about 20%-30% confluency of cells).

TABLE 2

| | | | Plate 1: With ORC (NuKnit ®) | | | |
|---|---|---|---|---|---|---|
| | 1 | 2 | 3 | 4 | 5 | 6 |
| A | Dox 0 μM ¼ Nuknit of 8 mm | Dox 0.1 μM ¼ Nuknit of 8 mm | Dox 0.5 μM ¼ Nuknit of 8 mm | Dox 5 μM ¼ Nuknit of 8 mm | Dox 25 μM ¼ Nuknit of 8 mm | Dox 50 μM ¼ Nuknit of 8 mm |
| B | Dox 0 μM ¼ Nuknit of 8 mm | Dox 0.1 μM ¼ Nuknit of 8 mm | Dox 0.5 μM ¼ Nuknit of 8 mm | Dox 5 μM ¼ Nuknit of 8 mm | Dox 25 μM ¼ Nuknit of 8 mm | Dox 50 μM ¼ Nuknit of 8 mm |
| C | Dox 0 μM ¼ Nuknit of 8 mm | Dox 0.1 μM ¼ Nuknit of 8 mm | Dox 0.5 μM ¼ Nuknit of 8 mm | Dox 5 μM ¼ Nuknit of 8 mm | Dox 25 μM ¼ Nuknit of 8 mm | Dox 50 μM ¼ Nuknit of 8 mm |
| D | GM only | GM only | GM only | No Cells (Blank) | No Cells (Blank) | No Cells (Blank) |

TABLE 3

| | | | Plate 2: Without ORC (NuKnit ®) | | | |
|---|---|---|---|---|---|---|
| | 1 | 2 | 3 | 4 | 5 | 6 |
| A | Dox 0 μM | Dox 0.1 μM | Dox 0.5 μM | Dox 5 μM | Dox 25 μM | Dox 50 μM |
| B | Dox 0 μM | Dox 0.1 μM | Dox 0.5 μM | Dox 5 μM | Dox 25 μM | Dox 50 μM |
| C | Dox 0 μM | Dox 0.1 μM | Dox 0.5 μM | Dox 5 μM | Dox 25 μM | Dox 50 μM |
| D | GM only | GM only | GM only | No Cells (Blank) | No Cells (Blank) | No Cells (Blank) |

The plates were incubated overnight, for 16-18 hours, in a water jacketed 37° C. incubator with 5% $CO_2$.

Day 2: Preparation of Dox-medium for plates: 58.3 μl Dox at 17.24 mM were added into 20 ml Growth medium to obtain a stock of 50 μM. This 50 μM stock, together with growth media, was used to prepare, 25 μM, 5 μM, 0.5 μM and 0.1 μM Dox.

The cells at this stage were about 40%-50% confluent. The plate's medium was decanted and replaced with 1 ml of the growth medium only or Dox medium prepared as described in above and according to the plate layout shown in Tables 2 and 3 above.

Immediately, a NuKnit® ¼ punch was added to the wells according to the plate layout.

The plates were incubated overnight, for 16-18 hours, in a water jacketed 37° C. incubator with 5% $CO_2$.

Day 3: The untreated cells at this stage were about 60%-70% confluent. The plate's medium was decanted and replaced with 0.5 ml of Growth medium. 50 µl of WST-1 were added to each well. The plates were then incubated for an additional 4 hours.

The plates were then read with an ELISA reader at 450 nm and 650 nm Optical Density (OD). Wells containing medium with no cells were used as blank.

Evaluation of the Results:

The results obtained by ELISA reader at 650 nm were subtracted from the results obtained at 450 nm per each well separately=sample OD.

For an OD graph: an average and SD of the sample OD of all repeated results were calculated and depicted in FIG. 1. Samples with 0 µM Dox without a NUKNIT® patch are essentially the same as Growth medium only and therefore all these results (n=9) were averaged together=0 µM Dox without NuKnit®.

For a relative viability graph: In order to evaluate the relative viability compared to untreated cells, the average sample OD of the GM only wells and 0 µM Dox wells was calculated=untreated OD. The relative viability of the rest of the wells was calculated according to the following calculation: sample OD/untreated OD×100. The results were depicted in FIG. 2.

Example 3

The Effect of Dox with or without ORC on Cell Viability

The following experiment was set in order to evaluate the effect of ORC on Doxorubicin activity on Normal Human Dermal Fibroblast (NHDF) cells. Doxorubicin activity will be expressed in relative cell viability compared to untreated cells. NHDF cells were incubated with a range of Dox concentrations with or without ORC in the medium. The final viability of the cells was evaluated with WST-1 staining. WST-1 is a Tetrazolium salts that is only cleaved to Formazan in metabolically active intact cells. The effect of a constant amount of ORC and increasing concentrations of Dox on NHDF cells viability was explored.

Figure 2:
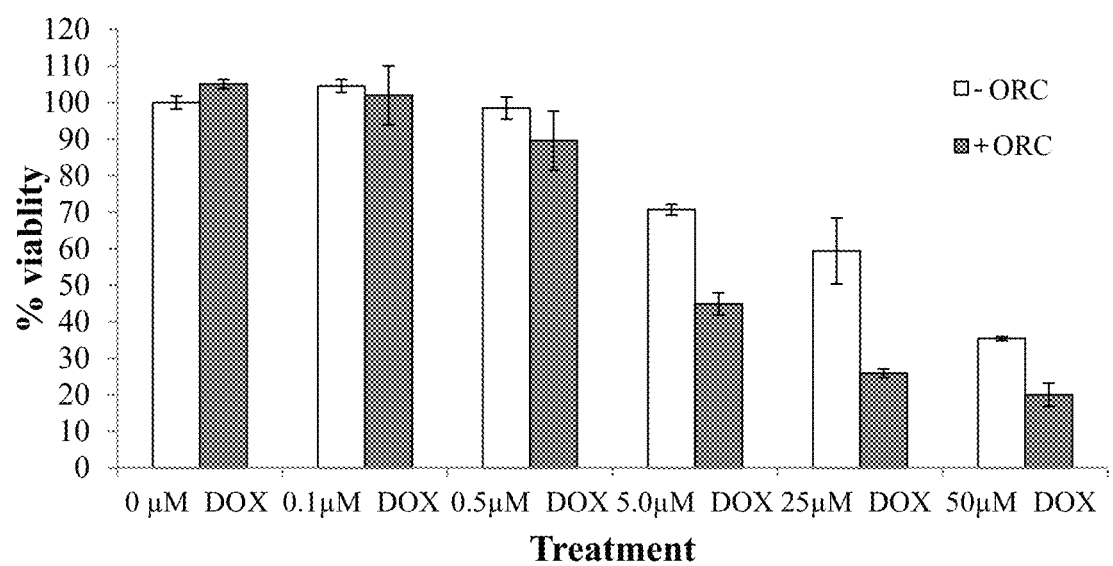
FIG. 2 shows the relative viability (%) of NHDF cells following treatment with increasing concentrations of Doxorubicin (Dox) in the absence or presence of ORC. Viability of the cells was evaluated with WST-1 staining.

The results in Table 4 and FIGS. 1 and 2 show that Dox reduces the viability of NHDF cells, in the absence of ORC in a dose dependent manner. The viability reduction of Dox is already evident at 5.0 µM Dox.

At 5.0 µM Dox, about 30% reduction in viability was observed, at 25 µM Dox about 40% reduction in viability was observed, and at 50 µM Dox 65% reduction in viability was observed.

The results show that addition of ORC only (i.e. in the absence of Dox) showed no reduction in viability.

The results show that addition of a constant amount of ORC synergizes the activity of Dox.

For example, 5.0 µM Dox in the presence of ORC showed reduction in viability of about 55%, at 25 µM Dox in the presence of ORC about 74% reduction in viability was observed, and at 50 µM Dox in the presence of ORC 80% reduction in viability was observed.

The results show that ORC increases the relative viability reduction of Dox by about 1.2 to 1.9-folds.

TABLE 4

The calculated potency increase of Dox in the presence of ORC.

| Dox Concentration (µM) | Without ORC relative reduction of viability (%) | With ORC relative reduction of viability (%) | Potency increase of Dox in the presence of ORC* |
| --- | --- | --- | --- |
| 5 | 29.3 | 55.12 | 1.89 |
| 25 | 40.649 | 74.07 | 1.83 |
| 50 | 64.584 | 79.97 | 1.24 |

*Calculated by dividing the relative viability (%) with ORC to the relative viability (%) without ORC.

The invention claimed is:

1. A method of treating cancer in a subject in need, the method comprises using a glycolytic dependent compound to be administered to the subject by a systemic route, the method comprises the steps of:
    A- targeting the glycolytic dependent compound to a cancerous tissue comprising one or more cancerous cells, by placing Oxidized Regenerated Cellulose (ORC) and/or Oxidized Cellulose (OC) in direct connection with the one or more cancerous cells, and
    B- administering the glycolytic dependent compound to the subject by systemic route,
    wherein the ORC and/or OC and the glycolytic dependent compound are administered in a non-blended form; wherein the ORC and/or OC and glycolytic dependent compound are administered by different administration routes; wherein the glycolytic dependent compound is administrated i) concurrently to the ORC and/or OC placing time, and/or ii) after the ORC and/or OC placing time.

2. The method according to claim 1, wherein the ORC and/or OC is placed in a non-bleeding site and/or in a non-resected site.

3. The method according to claim 1, wherein the ORC and/or OC is placed as an ORC and/or OC-coated surgical article.

* * * * *